US006440980B1

(12) United States Patent
Marcelletti et al.

(10) Patent No.: US 6,440,980 B1
(45) Date of Patent: *Aug. 27, 2002

(54) SYNERGISTIC INHIBITION OF VIRAL REPLICATION BY LONG-CHAIN HYDROCARBONS AND NUCLEOSIDE ANALOGS

(75) Inventors: John F. Marcelletti, San Diego; Laura E. Pope, Carlsbad; Mohammed H. Khalil, San Diego; David H. Katz; Lee R. Katz, both of La Jolla, all of CA (US)

(73) Assignee: Avanir Pharmaceuticals, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/265,922

(22) Filed: Mar. 10, 1999

Related U.S. Application Data

(63) Continuation-in-part of application No. 08/916,624, filed on Aug. 22, 1997, now Pat. No. 5,952,392.
(60) Provisional application No. 60/064,850, filed on Sep. 17, 1996, now abandoned.

(51) Int. Cl.[7] .................. A61K 31/52; A61K 31/054; A61K 31/70
(52) U.S. Cl. .................. 514/262; 514/43; 514/45; 514/46; 514/724
(58) Field of Search ............... 514/262, 724, 514/43, 45, 46

(56) References Cited

U.S. PATENT DOCUMENTS

| | | |
|---|---|---|
| 3,592,930 A | 7/1971 | Katz |
| 3,946,035 A | 3/1976 | Jacquet et al. |
| 3,987,198 A | 10/1976 | Young |
| 4,025,645 A | 5/1977 | Jelenko, III |
| 4,076,799 A | 2/1978 | Willer et al. |
| 4,186,211 A | 1/1980 | Debat |

(List continued on next page.)

FOREIGN PATENT DOCUMENTS

| | | | |
|---|---|---|---|
| EP | 0 875 233 A1 | 11/1998 | |
| FR | 2569108 | 9/1990 | |
| WO | WO8807866 | 10/1988 | |
| WO | WO90/04388 | 5/1990 | |
| WO | WO 94/05258 | 3/1994 | |
| WO | WO 95/16434 | 6/1995 | |
| WO | WO 95/27479 | 10/1995 | |
| WO | WO96/02244 | 2/1996 | |
| WO | WO 96/40144 | 12/1996 | |
| WO | WO 97/09978 | 3/1997 | |
| WO | 98/18472 | * 5/1998 | .......... A61K/31/52 |
| WO | WO 98/30244 | 7/1998 | |

OTHER PUBLICATIONS

CAPLUS Abstract, AN 1996:304119, Nakayama et al. 1996.*
Cooper et al. "Effect of fatty acids and alcohols on the penetration of acyclovir across human skin in vitro," 1985, Journal of Pharmaceutical Sciences, vol. 74, No. 6, pp. 688–689.*
Antonian, et al. (1987), AL721, A Novel Membrane Fluidizer, Neuroscience and Biobehavioral Reviews, 11, pp. 399–413.
Bazan, Nicolas G., (1989) The Metabolism of Omega–3 Plyunsaturated Fatty Acids in the Eye: The Possible Role of Docosahexaenoic Acid and Decosanoids in Retinal Physiology and Ocular Pathology, Prog. Clin. biol. Res., 312: pp. 95–112.

(List continued on next page.)

Primary Examiner—Russell Travers
Assistant Examiner—Shengjun Wang
(74) Attorney, Agent, or Firm—Knobbe, Martens, Olson & Bear, LLP

(57) ABSTRACT

The present invention is related to antiviral compositions comprising long-chain aliphatic compounds in combination with a nucleoside analog or phosphonoformic acid, in a pharmaceutically acceptable carrier. Methods for treating viral infections using such compositions are also disclosed.

46 Claims, 13 Drawing Sheets

U.S. PATENT DOCUMENTS

| | | | |
|---|---|---|---|
| 4,199,574 A | * | 4/1980 | Schaeffer ............... 514/262 |
| 4,200,655 A | | 4/1980 | Farah et al. |
| 4,258,029 A | | 3/1981 | Moloney et al. |
| 4,360,522 A | | 11/1982 | Schaeffer |
| 4,513,008 A | | 4/1985 | Revici et al. |
| 4,624,966 A | | 11/1986 | Yamamoto et al. |
| 4,670,471 A | | 6/1987 | Clark |
| 4,684,479 A | | 8/1987 | D'Arrigo |
| 4,865,848 A | | 9/1989 | Cheng et al. |
| 4,874,794 A | | 10/1989 | Katz |
| 4,879,109 A | | 11/1989 | Hunter |
| 4,880,634 A | | 11/1989 | Speiser |
| 4,900,555 A | | 2/1990 | Cheng et al. |
| 4,940,586 A | | 7/1990 | Cheng et al. |
| 4,950,688 A | | 8/1990 | Bowser et al. |
| 4,956,171 A | | 9/1990 | Chang |
| 5,030,448 A | | 7/1991 | Hunter |
| 5,070,107 A | | 12/1991 | Katz |
| 5,071,879 A | | 12/1991 | Katz |
| 5,104,656 A | | 4/1992 | Seth et al. |
| 5,154,855 A | | 10/1992 | Sekiguchi et al. |
| 5,166,219 A | | 11/1992 | Katz |
| 5,194,451 A | | 3/1993 | Katz |
| 5,194,654 A | * | 3/1993 | Hosteler ............... 558/152 |
| 5,208,257 A | | 5/1993 | Kabara |
| 5,216,142 A | | 6/1993 | Horrobin et al. |
| 5,276,020 A | | 1/1994 | Horrobin et al. |
| 5,380,754 A | | 1/1995 | Miller et al. |
| 5,436,234 A | | 7/1995 | Eibl |
| 5,534,554 A | | 7/1996 | Katz et al. |
| 5,567,816 A | | 10/1996 | Schloemer et al. |
| 5,580,571 A | | 12/1996 | Hostetler |
| 5,667,492 A | * | 9/1997 | Bologna et al. ............. 604/57 |
| 5,756,737 A | | 5/1998 | Turchetta et al. |

OTHER PUBLICATIONS

McBride et al., (1987) *Evaluation of Triacontanol–Containing Compounds as Anti–Inflammatory Agents Using Guinea Pig Models,* .

Katz et al., (1991) Antiviral activity of 1–docosanol, an inhibitor of lipid–enveloped viruses including herpes simplex, Proc. Natl. Acad. Sci. USA, 88: pp. 10825–10829.

Katz et al., n–Docosanol: Broad Spectrum Anti–Viral Activity against Lipid–enveloped Viruses, Annals N.Y. Acad. Sciences, 724: pp. 472–488.

Sandra, et al. (1979) Liposome–Cell Interactions, J. Biol. Chem. 254(7): pp. 2244–2249.

Sands, et al. (1979) Extreme Sensitivity of Enveloped Viruses, including Herpes Simplex, to Long–Chain Unsaturated Monoglycerides and Alcohols, Antimicrobial Agents and Chemotherapy, 15 (1): pp. 67–73.

Snipes, et al. (1977) Inactivation of Lipid–Containing Viruses by Long–Chain, Alcohols, Antimicrob. Agents & Chemother., 11: pp. 98–104.

Hostetler et al., (1997), Enhanced Oral Absorption and Antiviral Activity of 1–O–Octadecyl–sn–glycero–3–phospho–acyclovir and Related Compounds in Hepatitis B Virus Infection In Vitro, Biochem Pharmacol, 53; pp. 1815–1822.

Pope et al. (1996) Anti–herpes simplex virus activity of n–docosanol correlates with intracellular metabolic conversion of the drug, J. Lipid Res., 37: pp. 2167–2178.

Pope et al., (1998), The anti–herpes simplex virus activity of n–docosanol includes inhibition of the viral entry process, Antiviral Res., 40, pp. 85–94.

O'Brien et al., (1990) Nucleoside Metabolism in Herpes Simplex Virus–Infected Cells following Treatment with Interferon and Acyclovir, a Possible Mechanism of Synergistic Antiviral Activity, Antimicrob Agents Chemother, 34, pp. 1178–1182.

Hirsch et al., (1996), Antiviral Agents, In Fields Virology Third Edition pp. 431–466.

Oliver et al., (1985), Inhibition of HSV–Transformed Murine Cells by Nucleoside Analogs, 2'NDG and 2'–nor–cGMP: Mechanisms of Inhibition and Reversal by Exogenous Nucleosides, Virol, 145, pp. 84–93.

Franken et al., (1996), Epstein–Barr virus–driven gene therapy for EBV–related lymphomas, Nature Medicine, 2, pp. 1379–1382.

Caruso et al., (1995), Expression of a Tat–Inducible Herpes Simplex Virus–Thymidine Kinase Gene Protects Acyclovir–Treated CD4 Cells from HIV–1 Spread by Conditional Suicide and Inhibition of Reverse Transcription, Virol, 206, pp. 495–503.

Tyring et al., (1998), A Randomized, Placebo–Controlled Comparison of Oral Valacyclovir and Acyclovir in Immunocompetent Patients with Recurrent Genital Herpes Infections, Arch Dermatol, 134, pp. 185–191.

Blum et al., (1982), Overview of Acyclovir Pharmacokinetic Disposition in Adults and Children, Am. J. Med., 73, pp. 186–192.

* cited by examiner

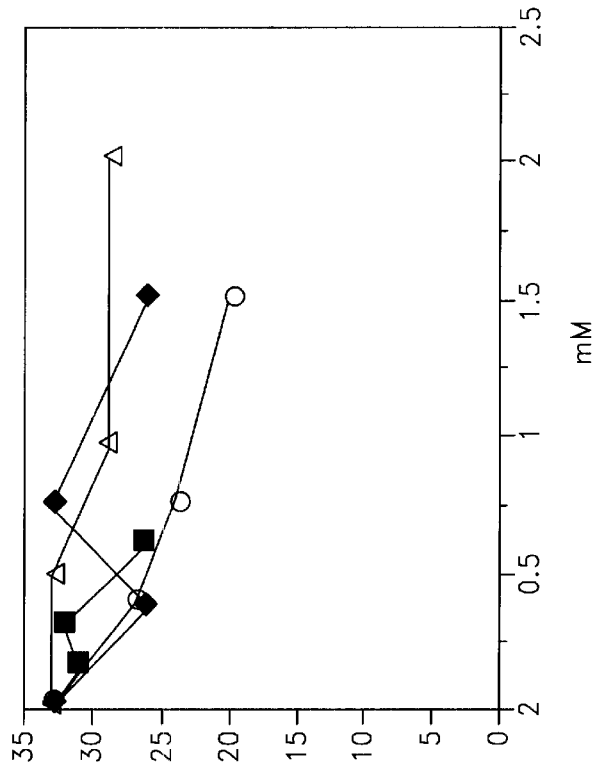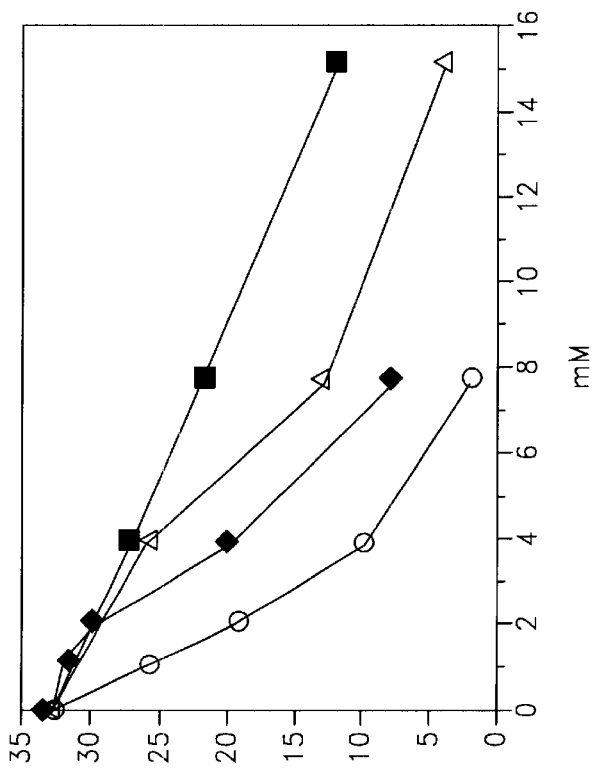

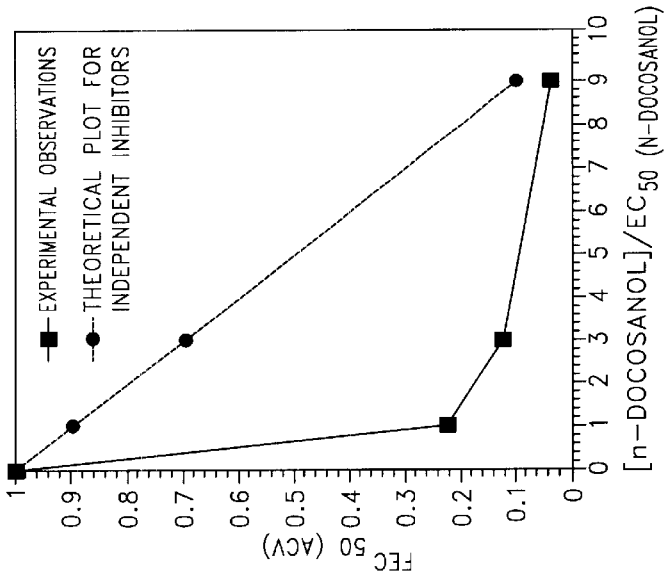
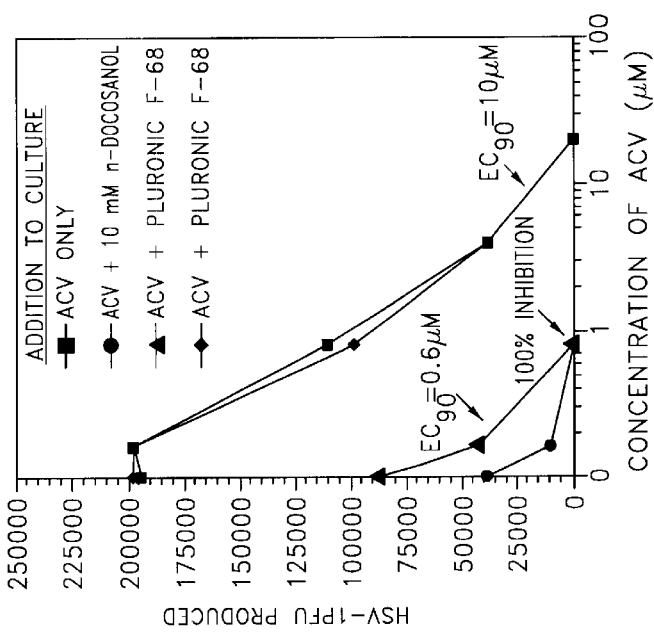
FIG. 10

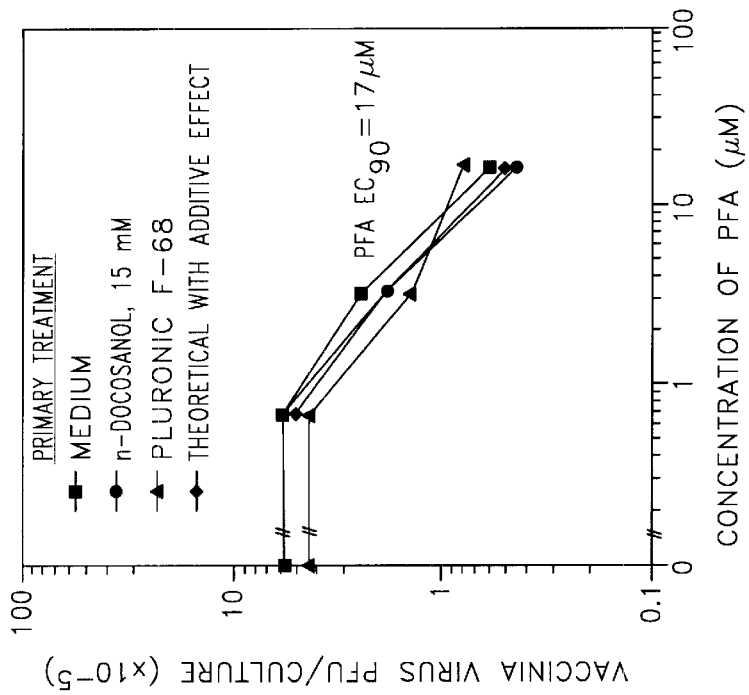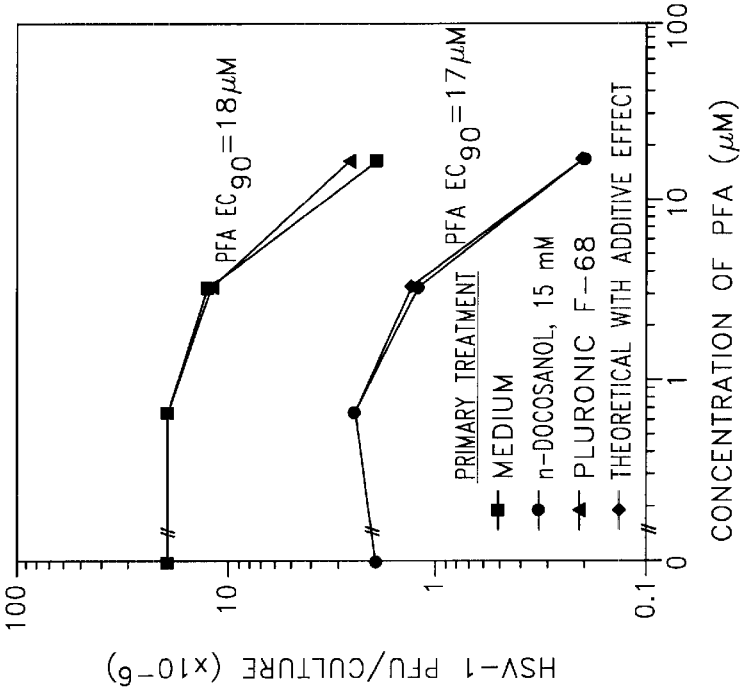
FIG. 12

SYNERGISTIC INHIBITION OF VIRAL REPLICATION BY LONG-CHAIN HYDROCARBONS AND NUCLEOSIDE ANALOGS

This is a continuation-in-part of patent application Ser. No. 08/916,624, filed on Aug. 22, 1997, now U.S. Pat. No. 5,958,392 which claims priority under 119(e) to Provisional Application No. 60/064,850 with a priority date of Sep. 17, 1996 now abandoned.

BACKGROUND OF THE INVENTION

This invention relates to treatment of viral infections using long-chain hydrocarbons in combination with nucleoside analogs, and more particularly to the topical application of therapeutic compositions containing n-docosanol in combination with a nucleoside analog or phosphonoformic acid (PFA).

Viral infections pose a serious threat to the public health. Viruses such as herpes simplex viruses (HSV-1 and HSV-2), cytomegalovirus (CMV), Epstein-Barr virus (EBV), varicella zoster virus (VZV), influenza viruses, human lymphotrophic viruses (e.g., HTLV-1) and human immunodeficiency viruses (e.g., HIV-1) result in significant morbidity and mortality. HSV-1 and HSV-2 are associated with inflammation and lesions of the skin and mucosal membranes, including cold sores, fever blisters and genital herpes lesions. VZV causes shingles and EBV is associated with mononucleosis. Influenza viruses cause flu symptoms and can be fatal. HIV causes acquired imnnunodeficiency that debilitates and kills infected individuals. Although these viruses may remain latent in some cells and for varying periods of time, generally viral replication results in irreversible destruction of the infected cell producing different clinical manifestations of the diseases they cause.

Most current antiviral therapies employ nucleoside analogs, such as the purine nucleoside analog, acyclovir (ACV), and the pyrimidine nucleoside analog, azidothymidine (AZT), which interfere with viral replication within infected host cells. These nucleoside analogs are converted to their triphosphorylated (nucleotide) derivatives by viral and/or cellular kinases, wherein they block viral DNA elongation. The guanine analog, 9-(2-hydroxy)-ethoxymethyl-guanine, referred to as ACV, possesses potent antiviral activity. Examples of therapeutic nucleoside analogs related to ACV and methods of preparing them are disclosed in U.S. Pat. Nos. 4,199,574, 4,294,831, and 4,360,522 to Schaeffer, U.S. Pat. No. 5,580,571 to Hostetler, U.S. Pat. No. 5,756,737 to Turchetta et al., and U.S. Pat. No. 5,567,816 to Schloemer et al.; the disclosures of which are incorporated herein by reference. The main problems involved in the use of these nucleoside analogs are their limited phosphorylation in some cells and the cytotoxic side effects of the nucleoside analog triphosphates. Moreover, these antiviral drugs can potentially act as mutagens and/or teratogens in host cells. Thus, despite the potent antiviral activities of the nucleoside analogs, less toxic, efficacious therapies have been sought.

Among the alternatives to the nucleoside analogs for treatment of viral infections, are a variety of long-chain alcohols, fatty acids, alkanes and related compounds. Early work with such compounds focused on their direct viricidal effects. For example, unsaturated alcohols having from 14 to 20 carbons and one to four double bonds have been reported to possess antiviral activity. The most effective of these unsaturated alcohols was γ-linolenyl alcohol, a C18 alcohol with double bonds at positions 6, 9 and 12 (Sands et al., *Antimicrob. Agents & Chemother.* 15:67–73, 1979). Compositions containing oleic acid (C18, one double bond) have also been shown to exhibit anti-herpes virus activity (PCT patent application WO 9602244A1).

Long-chain aliphatic alcohols having from 20 to 32 carbons have been shown to possess antiviral and anti-inflammatory activities. Therapeutic compositions containing such long-chain aliphatic alcohols and related compounds are described in U.S. Pat. Nos. 4,874,794, 5,071,879, 5,166,219, 5,194,451 and 5,534,554; the disclosures of which are incorporated herein by reference.

Some compounds that are structurally related to long-chain aliphatic alcohols have also been reported to possess antiviral activity. For example, U.S. Pat. No. 4,513,008 discloses the antiviral activity of C20 to C24 linear polyunsaturated acids, aldehydes or alcohols having five to seven double bonds. Compounds having a long chain fatty acyl group, containing at least three unsaturated bonds, attached to a nucleoside or nucleoside analog are also disclosed as antiviral treatments in U.S. Pat. No. 5,216,142. Related U.S. Pat. No. 5,276,020 discloses antiviral compounds having a C16, C18 or C20 long chain fatty acid group attached to a nucleoside analog and a method of treating virus infection using these compounds. Indeed, Hostetler et al. recently reported enhanced oral absorption and antiviral activity of a C18 derivative of ACV, 1-D-octadecyl-sn-glycero-3-phospho-ACV (Hostetler et al., *Biochem. Pharmacol.* 53:1815–1822, 1997).

Topical therapies comprising various alcohols, fatty acids and amines have also been reported. For example, antiviral activity was reported for liposomal AL721, a mixture of neutral glycerides, phophatidylcholine and phosphatidylethanolamine (Antonian et al., *Neurosci. Biobehav. Rev.* 11:399–413, 1987). Antimicrobial compositions for topical treatment containing a C15 glycerol monoester of lauric acid or a polyhydric alcohol monoester of lauric acid with a mixture of fatty acids (C10 capric and C8 caprylic acids) were disclosed in U.S. Pat. No. 5,208,257. Treatment of herpes lesions using topically administered compositions containing an anesthetic, a surfactant and a topical carrier were disclosed in U.S. Pat. No. 5,380,754. A method of treating inflammation by topically applying ethyl-cis,cis(9,12)octadecadienoate (ethyl linoleate) was disclosed in U.S. Pat. No. 4,025,645 as a cold sore treatment.

Katz et al. (*Proc. Natl. Acad. Sci. USA* 88:10825–10829, 1991; U.S. Pat. No. 5,534,554) have shown that one particular long-chain aliphatic alcohol, n-docosanol (C22), possess potent systemic and topical antiviral activity against a range of viruses, including herpes simplex virus (in vitro and in vivo), HIV-1 (in vitro), respiratory syncytial virus (in vitro) and Friend virus (in vitro and in vivo). Unlike C10 to C18 unsaturated alcohols which exhibit detergent-like antiviral activity, n-docosanol does not inactivate viruses directly (Katz et al., *Proc. Natl. Acad. Sci. USA* 88:10825–10829, 1991; Snipes et al., *Antimicrob. Agents Chemother.* 11:98–104, 1977). Progressive binding and uptake of n-docosanol by cells may account for its antiviral activity because pre-incubation of cells with the alcohol produces optimal antiviral activity. Moreover, 70% of cell-associated n-docosanol is found in cell membrane components and the remainder is associated with soluble cell fractions (Pope et al., *J. Lipid Res.* 37:2167–2178, 1996). Plasma membrane incorporation of n-docosanol does not inhibit virus binding to the cell surface. Early viral protein synthesis was inhibited by more than 80% and viruses did not localize to nuclei (Katz et al., *Proc. Natl. Acad. Sci. USA*

88:10825–10829, 1991). Fusion of the virus with the plasma membrane of the cell is inhibited (Pope et al., *Antiviral 'Res.* 40:85–94, 1998).

The inhibition of viral protein synthesis and antiviral activity of n-docosanol appears to require cellular metabolism of the alcohol (Pope et al., *J. Lipid Res.* 37:2167–2178, 1996; Katz et al., *Ann. N.Y Acad. Sci.* 724:472–488, 1994). Moreover, while intracellular metabolic conversions of n-docosanol may account for its antiviral activity (Katz et al., *Annals N.Y. Acad. Sciences,* 724:472–488, 1994), n-docosanol is not cytotoxic at concentrations up to 300 mM.

Compounds, such as n-docosanol, whose pharmacologic effects are mediated by cellular metabolism may alter the way a second drug may be metabolized and expressed. In addition, viruses are known to dramatically alter host cell metabolism. Such drug interactions can produce undesirable effects in patients being treated with multiple drugs. However, beneficial drug interactions can also occur. Indeed, there have been numerous reports about interactions between nucleoside analogs, such as ACV, and compounds which modulate cellular metabolism (Spector et al., *Proc. Natl. Acad. Sci. USA* 86:1051–1055,1989; O'Brien et al., *Antimicrob. Agents Chemother.* 34:1178–1182, 1990; Hirsch et al., 1996 *Antiviral agents.* In *Fields Virology* Third Edition, B. N. Fields, D. M. Knipe, P. M. Howley, eds. Lippincott-Raven Publishers, Philadelphia, pp. 431–466). Generally, the mechanism involves modulation of one or more steps in cellular nucleoside uptake or metabolism resulting in a more efficient expression of antiviral activity.

Because patients with recurrent herpesvirus disease could be concurrently treated with n-docosanol 10% cream and acyclovir (ZOVIRAX™, the potential for either detrimental or beneficial drug interactions was investigated. The present invention is based on the findings that n-docosanol synergistically intensified the antiviral activity of nucleoside analogs against replication of several herpesviruses and vaccinia virus.

SUMMARY OF THE INVENTION

The present invention is related to an antiviral composition comprising a long-chain aliphatic compound and a nucleoside or nucleotide analog or phosphonofoimic acid (PFA) in a pharmaceutically acceptable carrier. More particularly, the long-chain aliphatic compound is selected from the group consisting of C18–C28 primary alcohols, erucyl alcohol, brassidyl alcohol, n-docosane, n-docosanoic acid, erucamide and stearic acid, or mixtures thereof.

The alphatic compound is present at a concentration in a range of about 0.05% to about 40%. The nucleoside or nucleotide analog in the antiviral composition is selected from the group consisting of ACV, adefovir, azidothymidine, brivudin, cidofovir, ddC, ddI, famciclovir, ganciclovir, idoxuridine, lamivudine, lobucavir, penciclovir, ribavirin, sorivudine, trifluridine, trimethoprim, valaciclovir and Ara A. The nucleoside or nucleotide analog or PFA is present at a concentration in a range of about 0.1% to about 10%.

In a preferred embodiment, the antiviral composition also comprises a nonionic surfactant. The surfactant may comprise a difunctional block-polymer that is a polyoxyalkylene derivative of propylene glycol having a molecular weight of about 1,000 to about 25,000, a block copolymer of ethylene oxide and propylene oxide having a molecular weight of between 6,000 and 12,000, or the nonionic surfactant is octoxynol-9 or octoxynol-10.

Preferably, the antiviral composition of the present invention comprises n-docosanol and a nucleoside analog from the group consisting of ACV, or the pyrophosphate analog PFA, ribavirin, trifluridine, and Ara-A, in a pharmaceutically acceptable carrier, wherein the n-docosanol is present at a concentration in a range of about 0.05% to about 40% and the nucleoside analog is present at a concentration in a range of about 0.1% to about 10%.

A pharmaceutically acceptable carrier in accordance with the present invention comprises sucrose stearate in a concentration of about 1% to about 25%, mineral oil in a concentration of about 1% to about 25%, propylene glycol USP in a concentration of about 1% to about 25%, benzyl alcohol in a concentration of about 0.1% to about 10%, and water.

A method for treating a viral infection is also disclosed. The method comprises the administration of a composition comprising an aliphatic compound and a nucleoside analog or PFA in a pharmaceutically acceptable carrier, wherein the composition may be administered topically from three to five times per day, or parenterally, or via transmembranal penetration, the gastrointestinal tract, the respiratory system or the urogenital system.

In a preferred embodiment, the method for treating a viral infection comprises the administration of a composition comprising n-docosanol and either ACV, PFA, ribavirin, trifluridine or Ara-A in a pharmaceutically acceptable carrier.

It should be understood that both the foregoing general description and the following detailed description are exemplary and explanatory only and are not restrictive of the invention as claimed. The accompanying drawings illustrate various embodiments of the invention and, together with the description, serve to explain the principles of the invention.

BRIEF DESCRIPTION OF THE DRAWINGS

FIG. 2A is a diagram showing that increasing the ratio of surfactant to n-docosanol decreases viral plaque production when Vero cells are incubated with the suspension for 12 hours before adding HSV-2 virus; the surfactant:n-docosanol ratios were 1:1 (■), 3:1 (△), 5:1 (◇) and 10:1 (○).

FIG. 2B shows the corresponding controls as in FIG. 2A using the same concentration of surfactant in suspension as for each surfactant:alcohol ratio shown in FIG. 2A but without n-docosanol (using the same symbols as in FIG. 2A).

FIG. 10 shows synergistic inhibition by n-docosanol and ACV of HSV-1 production in Vero cell cultures. The data are expressed as mean PFU observed in triplicate initial cell cultures; standard errors did not exceed 15% of the respective mean (not shown).

FIG. 12 shows additive antiviral activity of n-docosanol and PFA against HSV-1 replication and no interaction against vaccinia virus. The data are expressed as mean PFU in quadruplicate cultures.

DETAILED DESCRIPTION OF THE PREFERRED EMBODIMENT

Figure 1:
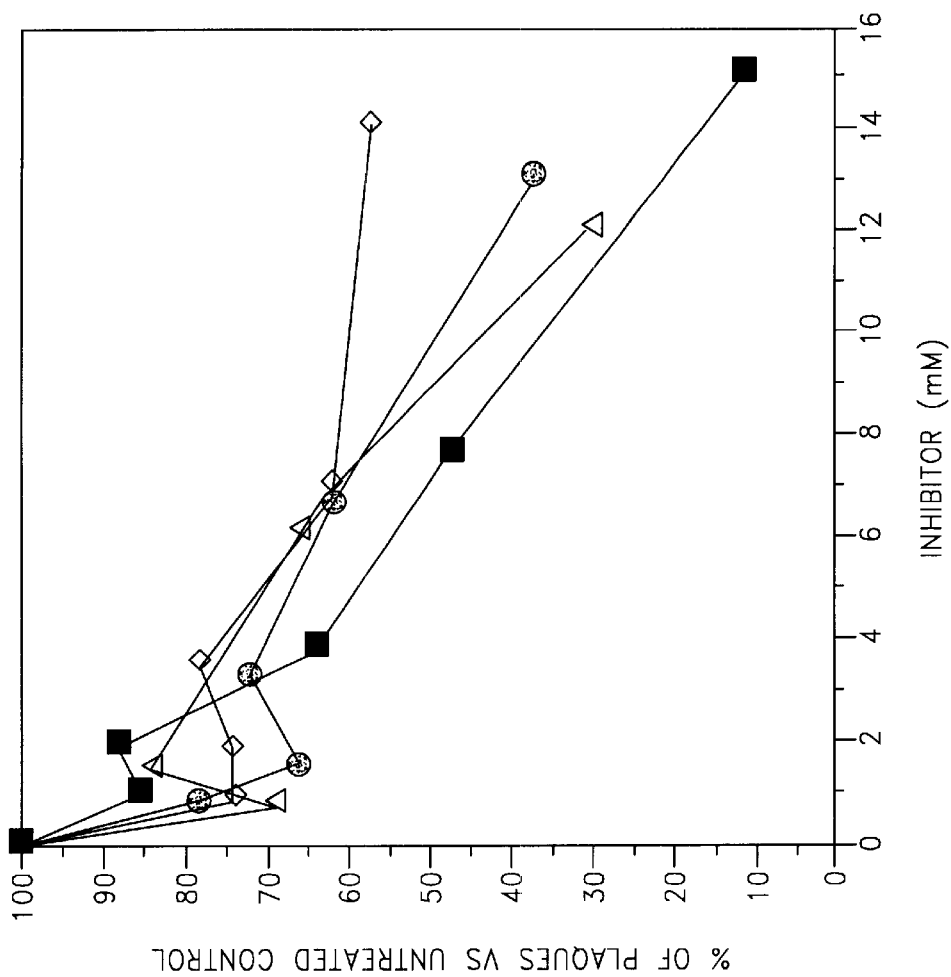
FIG. 1 is a diagram showing inhibition of HSV-2 plaque formation in Vero cells in vitro by suspensions of n-docosanol (C22, ■), n-tetracosanol (lignoceryl) alcohol (C24, ◇), n-hexacosanol (C26, ●) and n-octacosanol (C28, △) at the concentrations shown on the X-axis (data is percentage of plaques observed compared to control cultures exposed to surfactant suspensions lacking long-chain alcohol).

In its broadest embodiment, the present invention is a composition useful as a treatment for viral infections. The composition comprises a long-chain aliphatic compound in combination with a nucleoside or nucleotide analog or PFA in a pharmaceutically acceptable carrier. Also disclosed is a method for treating viral infections comprising the administration of a long-chain aliphatic compound in conjunction with a nucleoside or nucleotide analog or PFA.

The aliphatic compounds suitable for use in the present invention are selected from a group consisting of saturated aliphatic alcohols, mono-unsaturated aliphatic alcohols, aliphatic alkanes, mono-unsaturated aliphatic amides and aliphatic acids having a carbon chain length of 18 to 28 carbons (C18 to C28). The preferred composition includes stearyl alcohol, erucyl alcohol, brassidyl alcohol, arachidyl alcohol, n-docosanol, n-docosane, n-docosanoic acid, erucamide and stearic acid, or mixtures thereof. The aliphatic compound is most preferably n-docosanol. The aliphatic compound may be used according to a preferred variation of the present invention at concentrations in the range of about 0.05% to about 40%. Most preferably, n-docosanol is used at a concentration in the range of about 1% to about 20%.

Methods of synthesis of n-docosanol and erucyl alcohol (cis-13-docosen-1-ol) are known to those skilled in the art (e.g., see U.S. Pat. No. 4,186,211). Stearyl alcohol can be synthesized according to the method of Brown et al. (*J. Am. Chem. Soc.* 78:2582, 1956). Methods of synthesis of alkanes, aliphatic alcohols, amides and aliphatic acids are well known in the art (e.g., see A. Streitwieser, Jr. & C. H. Heathcock, *Introduction to Organic Chemistry*, 2nd ed., Macmillan Publishing Co., New York, N.Y., 1981, at pages 160, 243–247, 303–307, 311–312, 315–317, 401–406, 447–453, 515–516, 544, 548–555, 604–605, 670, 753–754 and 950).

The nucleoside or nucleotide analog in the antiviral composition of the present invention may be selected from the group consisting of ACV, adefovir, azidothymidine, brivudin, cidofovir, ddC, ddI, famciclovir, ganciclovir, idoxuridine, lamivudine, lobucavir, penciclovir, ribavirin, rifampin, sorivudine, trifluridine, valaciclovir and Ara A. The nucleoside analog or PFA is present at a concentration in a range of about 0.1% to about 10%. Most preferably, ACV, PFA, ribavirin, trifluridine or Ara-A is used at a concentration in the range of about 0.1% to about 10%.

Methods of synthesis of nucleoside and nucleotide analogs in accordance with the present invention are well known in the art. Acyclovir syntheses are disclosed in U.S. Pat. No. 4,199,574 to Schaeffer, U.S. Pat. No. 5,567,816 to Schloemer and U.S. Pat. No. 5,756,737 to Turchetta and are known to those skilled in the art.

Phosphonoformic acid may be synthesized by alkaline hydrolysis of triethyl phosphonoformate as described by Nylen, P. (*Chemische Berichte* 57:1023–1038, 1924).

The antiviral composition in accordance with one embodiment may include a surfactant that is a nonionic detergent such as a difunctional block-polymer that is a polyoxyalkylene derivative of propylene glycol having a molecular weight of about 1,000 to about 25,000 or greater. Preferably the surfactant is a block co-polymer of propylene oxide and ethylene oxide (poloxamer 188) having a molecular weight of between 6,000 and 12,000, more preferably about 8,400 (e.g., PLURONIC F-68®). Other preferred surfactants are octoxynol-9 and/or octoxynol-10 (e.g., TRITON X-100®), deoxycholate or mixtures of nonionic detergents. The active ingredients (long-chain aliphatic compound and nucleoside analog or PFA) comprise about 0.1% to about 50% by weight of the final composition, preferably 1% to 10% by weight. The optimum antiviral activity of the active ingredients depends on the ratio of surfactant to active ingredients which may range from 1:1 (w:w) to 10:1 (w:w), and preferably is 5:1 (w:w).

The active agents and optional surfactants are combined with a carrier that is physiologically compatible with the skin and membrane tissue of a human or animal to which it is administered. That is, the carrier is substantially inactive except for surfactant properties used in making a suspension of the active ingredients. The compositions may include other physiologically active constituents that do not interfere with the efficacy of the saturated aliphatic alcohols, mono-unsaturated aliphatic alcohols, aliphatic alkanes and aliphatic acids or nucleoside analogs. An exemplary composition is disclosed in U.S. Pat. No. 3,592,930.

Suitable carriers include aqueous and oleaginous carriers such as, for example, white petrolatum, isopropyl myristate, lanolin or lanolin alcohols, mineral oil, sorbitan monooleate, propylene glycol, cetylstearyl alcohol (together or in various combinations), with a detergent (e.g., polyoxyl stearate or sodium lauryl sulfate) and mixed with water to form a lotion, gel, cream or semi-solid composition. Other suitable carriers comprise mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. Preservatives may also be included in the carrier including methylparaben, propylparaben, benzyl alcohol and ethylene diamine tetraacetate salts. Dilute suspensions without thickeners are most suitable for delivery to skin surfaces as aerosol sprays, using well known methods of delivery. The composition may also include a plasticizer such as glycerol or polyethylene glycol (molecular weight 800 to 20,000) and penetration enhancers, such as azone. The composition of the carrier can be varied so long as it does not interfere with the pharmacological activity of the active ingredients.

The compositions may also include anti-microbial agents, other antiviral agents, anti-fungal agents, antioxidants, buffering agents, sunscreens and cosmetic agents such as coloring agents, fragrances, lubricants and moisturizers or drying agents. Anti-microbial agents useful for inclusion in the compositions include polymyxin B and tetracycline. Other antiviral agents included in the formulations may be cytokines. Anti-fungal agents that may be included are micatin or tolnaftate. Antioxidants such as vitamin E may be included. Sunscreens such as para-aminobenzoic acid may be included. Drying agents that may be included are well known, such as, for example, phenol and benzyl alcohol. Lubricants such as synthetic or natural beeswax may also be included. Thickening agents added to the compositions may include pullulin, xanthan, polyvinylpyrrolidone or carboxymethylcellulose.

Optimally the compositions effectively reduce the viral titer overall in the treated individual, particularly for systemic treatment, and in lesions, particularly for topical treatment of affected areas of the skin or mucous membrane. The disclosed methods of treatment also reduce symptoms of viral infection (e.g., pain associated with viral-caused lesions) and promote more rapid healing than seen without treatment.

The method of the present invention includes administration of a composition containing active ingredients and optionally a surfactant to a human or animal to treat or prevent viral infection. Administration is preferably to the skin or a mucous membrane using a cream, lotion, gel, ointment, suspension, aerosol spray or semi-solid formulation (e.g., a suppository), all formulated using methods well known in the art. However, parenteral and transmembrane penetration are also contemplated in accordance with some embodiments of the present invention. Where topical or transmembrane penetration are employed as a route of administration, the composition may optionally contain a penetration enhancer well known in the art, such as azone and dimethylsulfoxide. Applications consist of one to ten applications of 10 mg to 10 g per application for one to fourteen days. Applications are generally once every twelve hours and up to once every four hours. Most preferably, two to five applications of the composition per day, of about 0.1 g to 5 g per application, for one to seven days are sufficient to prevent or treat a viral infection. For topical applications, the compositions are preferably applied to lesions daily as soon as symptoms (e.g., pain, swelling or inflammation) are detected.

The compositions and methods are useful for preventing or treating a variety of viral infections such as those caused by herpesviruses including HSV-1, HSV-2 and HSV-6, CMV, EBV and VZV, by influenza viruses, human lymphotrophic viruses (e.g., HTLV-1), human immunodeficiency viruses (e.g., HIV-1), papilloma virus and respiratory syncytial virus. Because of the cytostatic activity of some of the compositions and the potential interactions with nucleoside analog anticancer drugs, the compositions and methods may also be useful for inhibiting malignant cell growth and/or metastasis. This cellular inhibition and combination chemotherapy can be combined with well known treatments for cancer (e.g., irradiation and/or surgery) to lead to total or partial remission of a tumor or other cancerous cell growth.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

Working Examples

Source of chemicals and reagents—n-Docosanol (>98% pure, mw 326) was purchased from M. Michel and Company, Inc., New York, N.Y. Benzyl alcohol, mineral oil, propylene glycol, stearic acid, and sucrose stearate were obtained from Croda Inc., New York, N.Y. Acyclovir powder was obtained from Burroughs Wellcome Co., Research Triangle Park, N.C. Adenine 9-β-D-arabinofuranoside, phosphonoformic acid, ribavirin, rifampicin, and trifluridine deoxyriboside were purchased from Sigma Chemical Co., St. Louis, Mo. PLURONIC F-68® (poloxamer 188) was purchased from BASF, Parisappany, N.J.

Source of animals, viruses, cell lines—The MacIntyre strain of HSV-1 (#VR-539), the MS strain of HSV-2 (#VR-540), The Ellen strain of varicella zoster virus (VZV, #VR-1367), the Towne strain of cytomegalovirus (CMV, #VR-977), and the WR strain of vaccinia virus (#VR-119) were obtained from the American Type Culture Collection (ATCC), Rockville, Md. Stocks of HSV and vaccinia virus were prepared in Vero cell (African Green monkey kidney, ATCC #CCL-81) cultures, while stocks of VZV and CMV were generated in the MRC-5 human embryonal lung cell line (ATCC #CCL-171). The levels of plaque forming units (PFU) for these viruses were determined in the cell line of origin and the stocks were stored at −85° C.

Methods of preparing the antiviral composition—Unless otherwise indicated, the topical cream emulsion of n-docosanol used in the working examples was prepared with (on a % w/w basis) 10% n-docosanol, 5% sucrose stearate, 8% mineral oil, 5% propylene glycol USP, 2.7% benzyl alcohol, and the remainder water (Katz et al., In *Slow Infections of the Central Nervous System. Ann. N.Y. Acad. Sci.* 724:472–488, 1994). The control vehicle for the cream contained 10% stearic acid so that a total of 10% aliphatic hydrocarbon was present. The constituents were heated to 80° C. and mixed while cooling to room temperature. The mixture typically congeals when the temperature has dropped to 30° C. On each treatment day, 0.3 ml of freshly reconstituted ACV (with water) was mixed with 2.7 ml n-docosanol-containing cream resulting in a 5% ACV and a 9% n-docosanol preparation; the corresponding control creams were mixed with 0.3 ml water. The mixtures were blended for 5 minutes in a SPEX vial (SPEX Industries, Inc., Metuchen, N.J.) using the SPEC Mixer.

n-Docosanol was also suspended in PLURONIC F-68® (poloxamer 188; Mr 8400) as described (Katz et al., *Proc. Natl. Acad. Sci. USA* 88: 10825–10829, 1991; Pope et al., *J. Lipid Res.* 37:2167–2178, 1996). PLURONIC F-68® was diluted to 12 mM in sterile saline at 37° C., and then heated to 50° C. n-Docosanol was added to the PLURONIC F-68® solution to 90 mM and the mixture was sonicated with a Branson 450 sonifier (Branson Ultrasonics, Danbury, Conn.) for 21 min at an output of 65 W; this warms the mixture to 86° C. The resulting suspension consists of very fine globular particles with an average size of 0.1–0.5 microns as measured by transmission electron microscopy (Katz et al., *Proc. Natl. Acad. Sci. USA* 88: 10825–10829, 1991). The control vehicle for this suspension contained only PLURONIC F-68® in saline.

Methods for optimizing antiviral activity—Antiviral activity of pharmaceutical compositions comprising a long-chain aliphatic compound and a nucleoside analog were optimized using four different assays, including (1) HSV infection of guinea pig skin, (2) HSV plaque formation, (3) numbers of herpesvirus-infected cells, and (4) inhibition of progeny virus production.

An in vivo assay system used hairless guinea pigs (250–400 gm) that were obtained from Charles River Laboratories, Wilmington, Mass. Their backs were cleaned with ethanol and sterile saline and inoculated with HSV-2 under general anesthesia using Ketamine (Parke-Davis, Morris Plains, N.J.) and Nembutal (Abbott Laboratories, North Chicago, Ill.). Saline (75 µl) containing $5\times10^5$ PFU of HSV-2 was applied to 4 cm×4 cm sites on the backs of guinea pigs followed by inoculation with a tattoo instrument. This is a generally accepted experimental method for evaluation of topical therapy in the treatment of HSV-mediated cutaneous disease (Spruance et al., *Antiviral Res.* 9:295–313, 1988). Each animal had 6 inoculation sites. Treatment with 200 µl of cream was applied with a glass rod with gentle circular rubbing 2 times/day. The sites were evaluated for numbers of vesicular lesions at the indicated time points.

The in vitro plaque formation assay for HSV was conducted using Vero cells plated at $1.5\times10^5$/ml in 16-mm wells (1 ml) or in 35-mm wells (2 ml) in DMEM supplemented with 5% fetal calf serum, 1 mM Na pyruvate, 4 mM L-glutamine, 50 Units/ml penicillin, 50 mg/ml streptomycin, and 10 mM HEPES buffer. Varying concentrations of n-docosanol suspension, or the corresponding control vehicle (lacking n-docosanol) were added at the outset of the culture. After 24 hours incubation, the test antiviral drug (e.g., ACV) was added and then all of the cultures were inoculated with the required PFU of HSV. The cultures were incubated (10% $CO_2$ in air; humidified) for additional 44 hours, stained (the staining/fixative consists of 1.25 mg/ml of carbol-fuchsin plus 2.5 mg/ml of methylene blue in methanol), and scored for HSV-induced plaques using a dissecting microscope (10×magnification).

The in vitro virus production assays for HSV and vaccinia virus were initiated as described for HSV plaque formation in Vero cells in 16-mm wells, but the plates were incubated a total of 3 days after inoculation with 500 PFU/well of the virus as indicated. At that time point, the culture supernatant fluids were harvested and diluted into fresh Vero cell cultures ($1\times10^5$/ml, 0.1 ml/well of a 96-well plate) to assay for PFU content. These secondary plates were incubated 72 hours before fixation, staining, and scoring for HSV cytopathology.

The assays for CMV and VZV infection were initiated with MRC-5 cells as described above for HSV PFU production in 16-mm wells. Two days after infection the culture medium was replaced with fresh medium lacking inhibitor. After an additional 2 days incubation, the cell were harvested by trypsinization and assayed for infected cells in an infectious center assay using MRC-5 cells. Briefly, the trypsinized cells were diluted into MRC-5 cell cultures in 24-well plates. After 6 days incubation, the secondary cultures were stained and scored for VZV and CMV cytopathology.

EXAMPLE 1

Antiviral Activity of C21 to C28 Aliphatic Alcohols

Aliphatic alcohols were suspended in the surfactant PLURONIC F-68® using the following procedure described for the alcohol n-docosanol. The surfactant was diluted to 10 mg/ml in 37° C. Dulbecco's high-glucose modified Eagle's medium (DMEM; Whittaker Bioproducts, Walkersville, Md.), and the solution was heated to 50° C. n-Docosanol was added to a final concentration of 30 mM to the surfactant solution and the mixture was sonicated for 21 min at an initial output of 65 W using a sonifier (Branson 450) causing the suspension to heat to 88° C. The resulting suspension contains globular particles of about $0.3\mu$ average size as determined by transmission electron microscopy. Control solutions containing PLURONIC F-68® with no added aliphatic alcohol and suspensions containing different concentrations of surfactant and/or n-docosanol were prepared using essentially the same procedure.

Suspensions of stearyl alcohol (C18), arachidyl alcohol (C20), heneicosanol (C21), lignoceryl alcohol (C24), and n-hexacosanol (C26) were prepared using essentially the same protocol as described for n-docosanol suspensions. For aliphatic alcohols longer than C22, the mixtures were heated before sonication to 80° C. for lignoceryl alcohol (C24) and 90° C. for n-hexacosanol (C26) and I-octacosanol (C28). n-Hexadecanol was obtained from Aldrich Chemicals Milwaukee, Wis.); stearyl alcohol and arachidyl alcohol were from M. Michel (New York, N.Y.) and the other compounds were from Sigma Chemical Co. (St. Louis, Mo.).

The MS strain of Herpes simplex virus 2 (HSV-2; from the American Type Culture Collection, Rockville, Md.; ATCC No. VR-540) was used to infect African Green monkey kidney cells (Vero cells; ATCC No. CCL 81) to determine the effects of aliphatic alcohol suspensions on efficiency of plaque formation. Vero cells were cultured using $6\times10^5$ cells in 1.8 ml medium per 35-mm well or $3\times10^5$ cells in 0.8 ml medium per 16-mm well in DMEM supplemented with 5% fetal calf serum, sodium pyruvate, L-glutamine, penicillin/streptomycin and 1 mM Hepes buffer at 37° C. in a humidified incubator containing 10% $CO_2$. Control surfactant suspensions or suspensions containing aliphatic alcohols were added at the outset of the culture. After 24 hr, HSV-2 virus was added to the cultures using 175 pfu/35-mm well and or 50 pfu/16-mm well.

After about 42 hr from addition of HSV-2, cultures were washed once with a physiological saline solution. The cells were fixed and stained with methanol containing carbol-Fuchsin (1.25 mg/ml) and methylene blue (2.5 mg/ml) and scored for plaques. The data presented are the mean of duplicate cultures, which generally varied by less than 10%, and statistical comparisons were made using Student's t-test.

The suspensions containing C21, C24, C26, or C28 aliphatic alcohols inhibited HSV-2 plaque production in Vero cells with dose response curves similar to that of n-docosanol (C22). Typical results are shown in FIG. 1. The effective concentrations (mM) required for 50% inhibition ($EC_{50}$) of plaque production are listed in Table 1.

There was no obvious chain length effect on inhibition of HSV-2 plaque formation. All the C21 to C28 alcohols inhibited HSV-2 plaque production and none of the compounds exhibited significantly greater activity than C22. The odd chain length compound, heneicosanol (C21), also inhibited plaque production by HSV-2 showing that there is no obvious chain length effect (i.e., odd chain length molecules functioned as well as even).

TABLE 1

Alcohol-Suspension Inhibition of HSV-2 Plaque Formation

| Carbon Chain Length | M.W. | 50% Inhibition* Concentration (mM) |
|---|---|---|
| 18 | 284.6 | Toxic** |
| 20 | 298.6 | Toxic** |
| 21 | 312.6 | 16.0 |
| 22 | 326.6 | 8.6 |
| 24 | 354.6 | 14.1 |
| 26 | 382.6 | 8.4 |
| 28 | 410.6 | 10.5 |

*Percent inhibition of plaque formation by HSV-2 added to Vero cells after 12 hr incubation of cells with the indicated alcohol was plotted as a function of alcohol concentration and the amount required for 50% inhibition was determined by linear regression.
**"Toxic" means the cell monolayer was destroyed by the end of a 12-hour incubation period with a suspension containing at least 1.5 mM of the alcohol; at non-toxic concentrations no significant antiviral activity was recorded.

The suspensions of stearyl alcohol (C18) and arachidyl alcohol (C20) were toxic to Vero cells when added in amounts where viral inhibitory activity was observed with n-docosanol. At concentrations that were not cytotoxic (0.2 $\mu$M for stearyl alcohol and 2 $\mu$M for arachidyl alcohol), equivalent concentrations of the C18 and C20 aliphatic alcohols showed no inhibition of viral plaque production. Control suspensions of surfactant lacking an aliphatic alcohol were not cytotoxic and did not exhibit antiviral activity.

EXAMPLE 2

Effects of Increasing the Ratio of Surfactant to Aliphatic Alcohol

The antiviral effect of increasing the ratio (w:w) of surfactant to aliphatic alcohol was demonstrated using increasing ratios of PLURONIC F-68® to n-docosanol (compare to Example 1 using a 1:1 (w:w) ratio of surfactant to alcohol). The 1:1 suspension has a molecular ratio of 26:1 for n-docosanol (molecular weight 326.57) to surfactant (molecular weight 8,400) molecules. Generally, increasing the amount of surfactant decreases the particle size in suspension and causes formation of smaller unilamellar, rather than multilamellar, vesicles (Sandra et al., *J. Biol. Chem.* 254:2244–2249, 1979). This results in more of the alcohol occurring at the particle surface where it is available for interaction with cells.

Suspensions of n-docosanol were made essentially as described in Example 1 using a constant amount of the alcohol but increasing the amount of surfactant to achieve a 3:1, 5:1 and 10:1 (w:w) ratio of PLURONIC F-68® to n-docosanol in the final suspension. Increasing the surfactant to alcohol ratio increased the antiviral effectiveness of the suspension in Vero cell culture (FIG. 2). That is, the 3:1 surfactant to alcohol ratio suspension showed greater antiviral activity than the 1:1 ratio (at n-docosanol$\geq$8 mM); the 5:1 ratio suspension showed increased antiviral activity compared to the 1:1 ratio (at n-docosanol$\geq$4 mM); and the 10:1 ratio exhibited more antiviral activity compared to the 1:1 ratio (at n-docosanol$\geq$1 mM). The antiviral activity was dependent on the n-docosanol in the suspension because control cultures incubated with the same concentration of surfactant in suspension as for each of the ratio tested above showed essentially no antiviral activity (FIG. 2B).

The increased surfactant to alcohol ratio also correlated with an increase in the amount of cell-associated n-docosanol as determined using Vero cells incubated for 24 hours with surfactant-n-[1-$^{14}$C]docosanol suspensions. Cells incubated with suspensions containing a 4:1 ratio of surfactant to n-docosanol bound $7.8 \times 10^{-6}$ $\mu$g/cell, whereas an equivalent culture incubated with a 1:1 ratio suspension bound $3.1 \times 10^{-6}$ $\mu$g/cell. Optimal antiviral activity of n-docosanol was obtained with surfactant to alcohol ratios of about 4:1 to 5:1 (w:w).

The antiviral activity of the aliphatic compounds was not a property of a unique combination of the aliphatic compound and a particular nonionic surfactant in suspension. That is, other detergents produced effective antiviral suspensions of aliphatic alcohol. Suspensions of n-docosanol with a non-ionic octoxynol detergent (TRITON X-100®, Rohm & Haas) were prepared by: a) melting 2.5 g of n-docosanol with 1.5 g detergent at 90° C., b) mixing the melted solution with 500 ml saline at 90° C. and 1.15 g polyvinylpyrrolidone (PVP), c) processing the hot mixture through a microfluidizer at 1300 psi for 5 cycles, and d) ultrafiltering the processed mixture through a hollow fiber cartridge to eliminate excess detergent and PVP. A control detergent suspension was prepared in a similar manner except that n-docosanol was omitted. Deoxycholate suspensions of n-docosanol (surfactant to alcohol ratio of 1:1 by weight) were prepared essentially as described above.

Figure 3:
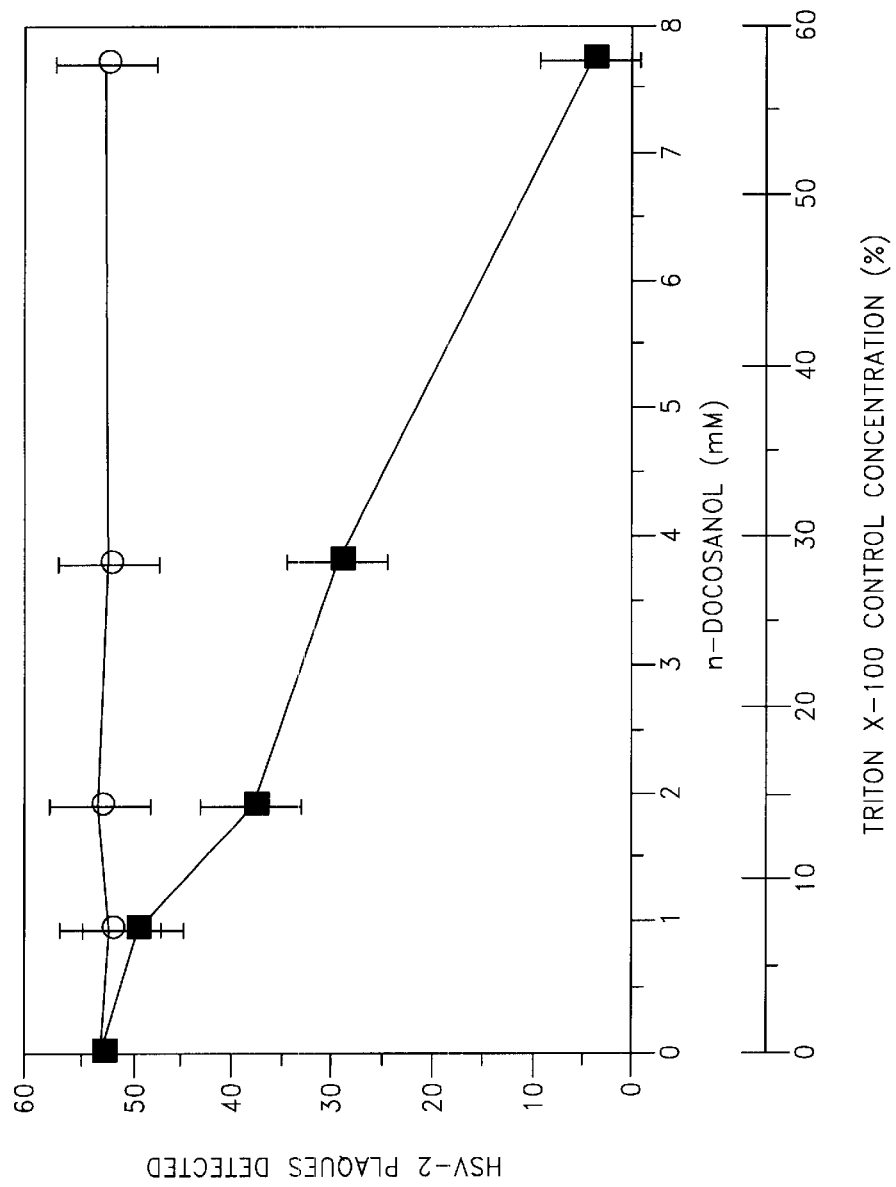
FIG. 3 is a diagram showing that octoxynol surfactant suspensions of n-docosanol (■) inhibit HSV-2 plaque formation in Vero cells incubated with the suspension and HSV-2 for 48 hours with increasing inhibition correlated with increasing concentration of n-docosanol, whereas control cultures incubated with HSV-2 and octoxynol surfactant (○) showed no inhibition (i.e., equivalent to untreated controls having about 50 plaques/well); bars above and below the data points show the standard deviation for duplicate samples.

Both the octoxynol and deoxycholate suspensions of the n-docosanol inhibited HSV-2 plaque production in the Vero cell assay. Typical results are shown in FIG. 3. The octoxynol/n-docosanol suspension inhibited plaque formation relative to the octoxynol control at n-docosanol concentrations of greater than or equal to 2 mM with an $EC_{50}$ of about 4.5 mM. The nonionic surfactant used to make an aliphatic alcohol suspension does not account for the suspension's antiviral activity.

Increasing the ratio of surfactant to n-docosanol significantly increased the antiviral activity of the suspension. That is, the amount of n-docosanol in the suspension required for 50% inhibition of plaque production decreased (e.g., from 15 mM to 3 mM).

EXAMPLE 3

Antiviral Activity of the Aliphatic Alkane, n-Docosane

A surfactant/n-docosane (Sigmna Chemical Co.) suspension was prepared essentially as described in Example 1. The antiviral activity of the surfactantin-docosane suspension was compared to that of a similar surfactantin-docosanol suspension using the Vero cell assay to measure inhibition of HSV-2 plaque formation essentially as described in Example 1.

Figure 4:
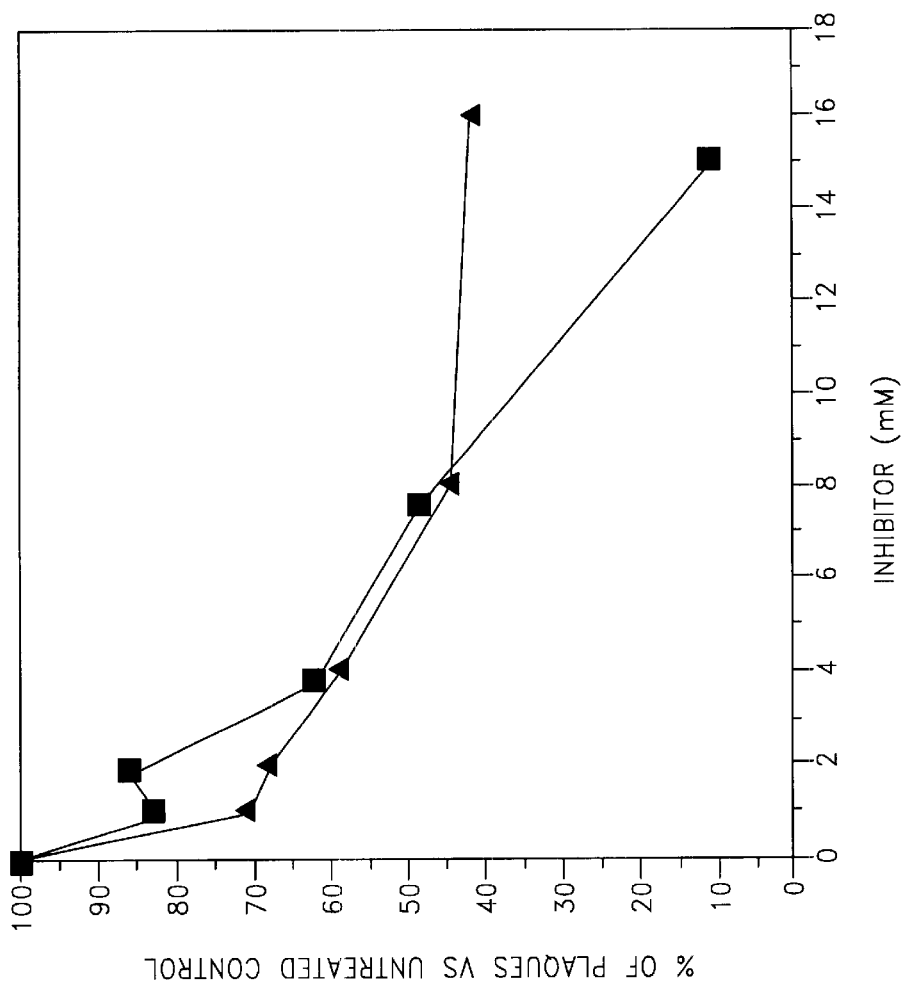
FIG. 4 is a diagram showing that suspensions of surfactant/n-docosanol (■) and surfactant/n-docosane (▲) inhibit HSV-2 viral plaque formation in cultured Vero cells incubated with the compounds for 12 hours before the addition of HSV-2.

As shown in FIG. 4, a surfactant/n-docosane suspension inhibited plaque production by HSV-2 in Vero cell cultures with a dose response curve similar to that of the surfactantin-docosanol suspension. PLURONIC F-68® suspensions of n-docosanol (■) and n-docosane (▲) inhibited HSV-2 viral plaque formation in cultured Vero cells incubated with the suspensions for 12 hours before the HSV-2 addition. Control surfactant suspensions showed no antiviral activity (data not shown). Hence, both the C22 aliphatic alcohol and alkane exhibited comparable antiviral activity indicating that the hydroxyl moiety was not required for the activity as measured by inhibition of viral plaque formation.

EXAMPLE 4

Oxidation of the 1-hydroxyl Moiety of n-Docosanol Results in Cytotoxicity

A nonionic detergent surfactantin-docosanoic acid (Sigmna Chemical Co.) suspension was prepared and tested for antiviral activity using Vero cells and HSV-2 essentially as described in Example 1. The C22 fatty acid was toxic to Vero cells when used at concentrations equivalent to those at which viral inhibition occurs with n-docosanol (see Table 2). When suspensions of n-docosanoic acid at 4 mM to 15 mM were added to the cultures, the cells became rounded and detached from the plate. At tolerable concentrations of n-docosanoic acid ($\leq 2$ mM), the antiviral activity was approximately equal to that observed with n-docosanol suspensions at the same concentrations, but significantly less than that observed with 4 to 15 mM n-docosanol suspensions. Thus, the C22 fatty acid exhibits some antiviral activity at dilutions tolerable to cells but has increased cytotoxicity compared to the corresponding aliphatic alcohol.

TABLE 2

Percent Inhibition of Plaque Formation**

| Conc* | Docosanol | Docosane | Docosanoic acid | Erucyl Alcohol | Brassidyl Alcohol |
|---|---|---|---|---|---|
| 15 | 66 | 58 | Toxic† | Toxic | ND |
| 8 | 44 | 55 | Toxic | Toxic | 48 |
| 4 | 36 | 42 | Toxic | Toxic | 44 |
| 2 | 40 | 31 | 30 | Toxic | 35 |
| 1 | 14 | 28 | 16 | 93 | 27 |
| 0.5 | ND‡ | ND | 26 | 91 | ND |
| 0.25 | ND | ND | ND | 70 | ND |

*The mM concentrations of n-docosanol (m.w. 326.6), n-docosane (m.w. 310.6), n-docosanoic acid (m.w. 340.6) and erucyl alcohol (m.w. 324.6) in suspension with PLURONIC F-68 ® (m.w. 8,400) or brassidyl alcohol (m.w. = 324.6) in suspension with TETRONIC-908 ® (m.w. 25,000) in the Vero cell culture 12 hr before addition ofHSV-2 virus, except for erucyl and brassidyl alcohol suspensions which were added with the virus.
554 "Toxic" means the cell monolayer was destroyed within 24 hr after addition of the suspension at the concentrations of alcohol or acid shown in the first column.
555 "ND" means not determined.
**Inhibition was relative to a control infection of Vero cells to which no suspension was added. Another control was a surfactant suspension to which no active ingredient was added, which, when added to infected Vero cells, showed $\leq 5\%$ inhibition relative to viral infection of Vero cells with no suspension added.

EXAMPLE 5

Antiviral Activity of C22 Mono-unsaturated Aliphatic Alcohols

Surfactant/erucyl alcohol (cis-13-docosen-1-ol; Sigma Chemical Co.) suspensions were prepared and tested for antiviral activity using Vero cells and HSV-2 essentially as described in Example 1 to determine the effect of unsaturation of the hydrocarbon chain. The surfactant/erucyl alcohol suspension was toxic to Vero cells when added to cultures at concentrations where n-docosanol is effective (2–15 mM). However, as shown in Table 2, concentrations that were tolerable to the cells ($\leq 1$ mM) showed significant inhibition of HSV-2 plaque production (to 93%). Moreover, no cellular toxicity was observed at 1 mM erucyl alcohol. The effective concentration required to inhibit plaque formation by 50% for erucyl alcohol ($EC_{50}$=0.15 mM) was 60-fold lower than the concentration required for n-docosanol ($EC_{50}$=9 mM). The therapeutic index is greater than or equal to 6.7 (i.e., 1 mM/0.15 mM).

Similarly, the antiviral activity of the trans-isomer of the C22 mono-unsaturated alcohol, brassidyl alcohol (trans-13-docosen-1-ol) was determined. Suspensions were made with another non-ionic surfactant, TETRONIC-908® (BASF) and viral inhibition assays were performed with HSV-1 instead of HSV-2 using the procedures essentially as described in Example 1. As shown in Table 2, brassidyl alcohol exhibits antiviral efficacy similar to n-docosanol. The cellular toxicity of brassidyl alcohol was significantly less than that of erucyl alcohol.

Based on these results, the addition of a single cis (but not trans) double bond at position 13 of the C22 aliphatic alcohol greatly increased antiviral activity. The alcohol with the trans double bond was less toxic than the alcohol with the cis double bond. The increased cytotoxicity may result from the bend in the molecule resulting from the cis double bond.

Surfactant/erucyl alcohol suspensions did not have a direct virucidal effect. That is, incubation of the HSV-2 virus with the surfactant/erucyl alcohol suspension for 2 hours did not inactivate the virus as measured by subsequent plaque formation on Vero cells.

EXAMPLE 6

Erucamide Testing in Mammalian Cell Cultures

Erucamide (cis-13-docosenoamide; m.w.=337.59) is a C22 long-chain amide with a single double bond similar in structure to erucyl alcohol. A nonionic detergent surfactant/erucamide (Aldrich Chemical Co.) suspension was prepared with TETRONIC-908® and tested for antiviral activity using Vero cells and HSV-2 essentially as described in Example 1. The C22 amide was toxic to Vero cells when used at 3 mM or greater concentrations, similar to the toxicity seen with erucyl alcohol and n-docosanoic acid (see Table 2). When suspensions of erucamide at 3 mM to 15 mM were added to the cultures, the cells became rounded and detached from the plate. At lower concentrations of erucamide in the suspension, significant antiviral activity was seen. At tolerable concentrations of erucamide ($\leq 1.7$ mM), the antiviral activity of the erucamide suspension was less than essentially equivalent concentrations of suspensions of erucyl alcohol but greater than that of suspensions of n-docosanol, n-docosane, n-docosanoic acid or brassidyl alcohol. That is, the percent inhibition of plaque formation for erucamide suspensions was 78% at 1.7 mM, 68% at 1.5 mM, 58% at 1.2 mM, 44% at 0.89 mM, 42% at 0.59 mM and 34% at 0.03 mM. Thus, the C22 amide exhibits significant antiviral activity at dilutions tolerable to cells but has increased cytotoxicity relative to the C22 saturated aliphatic alcohol (n-docosanol) and similar to that seen with the corresponding C22 mono-unsaturated erucyl alcohol.

EXAMPLE 7

Cytotoxicity in Mammalian Cell Cultures n-Docosanol exhibits minimal cytotoxicity to cultured cells even with prolonged incubations. Three assays were used to quantitate the effects of aliphatic alcohols on cell survival and proliferation: 1) counting cells with a hemocytometer and determining the number of cells that exclude trypan blue; 2) measuring the incorporation of $^3$H-thymidine into cellular DNA by adding $^3$H-thymidine (from New England Nuclear) to the culture medium, lysing the cells with water and harvesting the DNA onto filter paper; and 3) measuring total cellular protein using a sulforhodamine assay adapted for use in 96-well microtiter plates (Skehan et al., *J. Natl. Cancer Inst.* 82:1107–1112, 1990). All of these methods are well known cell viability and cytotoxicity assays.

Cells tested include Vero (see Example 1), WI-38, a human embryonic diploid lung cell line (ATCC No. CCL 75), HFL1, a human fetal lung diploid cell line (ATCC No. CCL 153), and a human fetal foreskin (ATCC No. 1635). A murine B-cell hybridoma line (designated MBI-9) was constructed and cultured as described previously (Marcelletti et al., *J. Immunol.* 148:3857–3863, 1992) although other tumor lines and hybridomas such as any of the ATCC TIB or HB cell lines could be equivalently used to determine the effects of aliphatic compounds in suspension on cell proliferation. All cells were cultured in DMEM supplemented with 10% fetal calf serum, sodium pyruvate, L-glutamine and penicillin/streptomycin using procedures well known in the art. The suspensions of aliphatic alcohols were prepared essentially as described in Example 1.

Using the first assay, Vero cells were cultured up to 72 hours in the presence of 9 mM n-docosanol contained in surfactant suspensions without observable deleterious effects when cultures were inoculated at 6×10$^5$ cells in 1.8 ml medium per 3 5-mm well or 3×10$^5$ cells in 0.8 ml medium per 16-mm well. Typical data are presented in Table 3, showing that the total number of viable Vero cells and foreskin fibroblasts was unchanged after 24 hr to 72 hr incubation with the aliphatic alcohol suspension. The other cell lines tested, including normal skin fibroblasts (ATCC CRL 1900), WI-38 lung cells, human fetal lung cells and a B-cell hybridoma, exhibited similar cell viability in the presence of n-docosanol suspensions if cells were inoculated at relatively high densities. Control suspensions of surfactant without the aliphatic alcohol also showed no cytotoxicity for the Vero cells but exhibited a time dependent cytotoxicity for the fetal foreskin cells that was not observed with the alcohol-containing suspension. For the fetal foreskin cell line, the addition of the aliphatic alcohol apparently decreased the cytotoxic effects of the surfactant.

Although the cell lines remained impermeable to trypan blue even after 72 hours of incubation with n-docosanol, normal skin fibroblasts, foreskin fibroblasts, WI-38 cells and human fetal lung cells showed a detectable change in morphology when examined using light microscopy. After 72 hr incubation with the alcohol suspensions, numerous translucent areas appeared in the cells' cytoplasm and the cells appeared vacuolized. Cells treated with control surfactant suspensions did not appear vacuolized after 72 hrs incubation.

In contrast to lack of cytotoxicity generally seen with the n-docosanol suspensions, suspensions of stearyl alcohol (C18) and arachidyl alcohol (C20) were extremely cytotoxic to all cell lines tested. In the presence of these C18 and C20 aliphatic alcohols, cells growing in a monolayer detached from the plate and lysed. Suspended cells also lysed when exposed to the stearyl and arachidyl alcohol suspensions.

Figure 5:
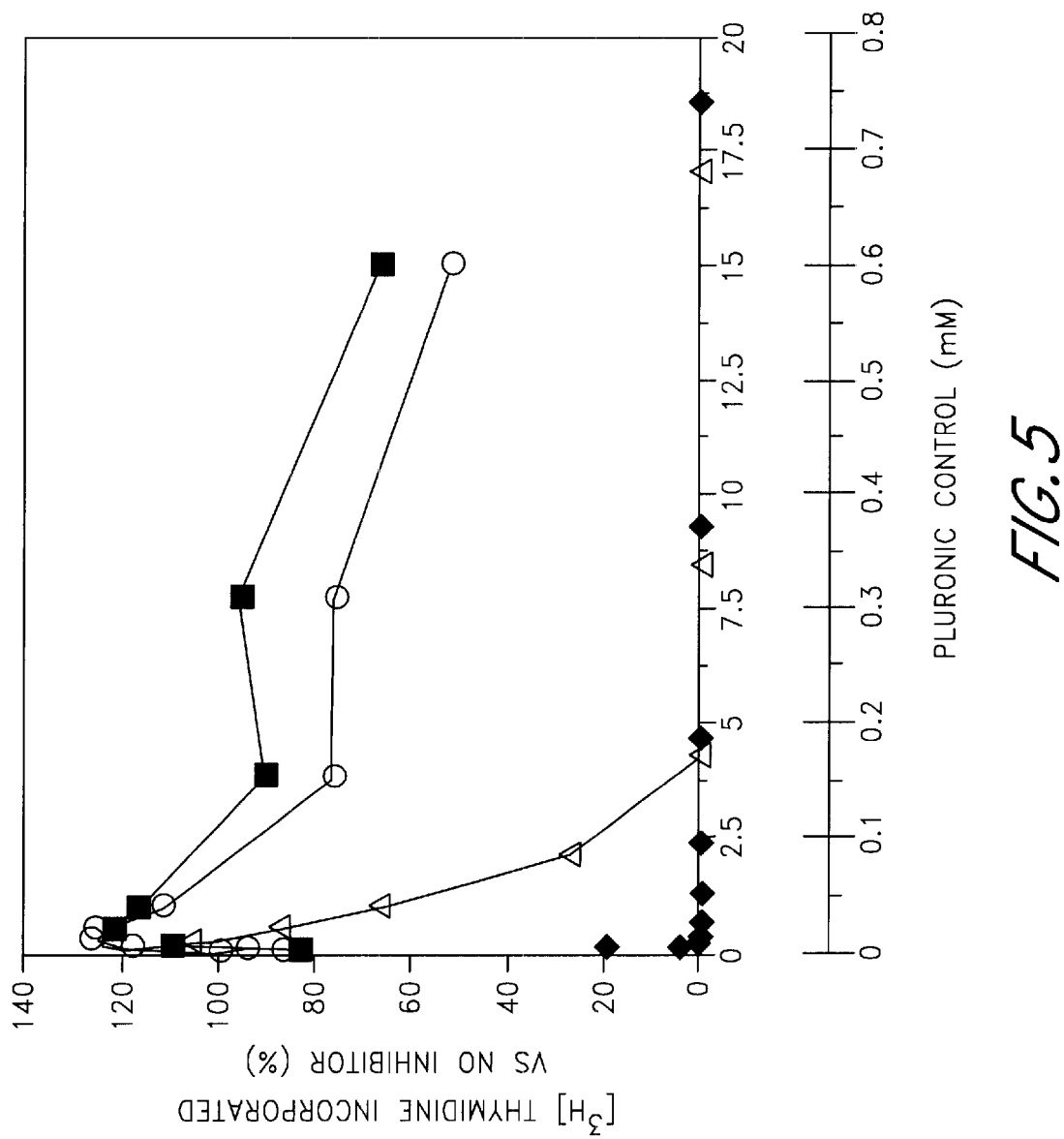
FIG. 5 is a diagram showing that suspensions of stearyl alcohol (C18, ♦) and arachidyl alcohol (C20, ∆) are toxic to cultured B-cell tumor cells incubated for 48 hours with the suspensions at the concentrations indicated on the X-axes compared to controls incubated with suspensions of surfactant without alcohol (○) as determined by $^3$H-thymidine incorporation into DNA (data is the percentage of controls incubated with media only).

Viability was quantified in a variety of cell lines either by measuring $^3$H-thymidine incorporation into DNA or by measuring total cellular protein by staining with sulforhodamine B. Typical results are illustrated in FIG. 5 showing inhibition of $^3$H-thymidine incorporation into DNA of a B cell hybridoma at different concentrations of the C18, C20 and C22 aliphatic alcohols. The IC$_{50}$ for stearyl alcohol (C18) for the B

TABLE 3

| | | Vero Cells | | Fetal Foreskin Cells | |
|---|---|---|---|---|---|
| Treatment* | Incubation (hr) | No. Viable** | % Control*** | No. Viable** | % Control*** |
| n-docosanol + surfactant | 24 | 7.48 × 10$^5$ | 101 | 2.41 × 10$^5$ | 131 |
| n-docosanol + surfactant | 48 | 8.69 × 10$^5$ | 137 | 2.78 × 10$^5$ | 118 |
| n-docosanol + surfactant | 72 | 8.61 × 10$^5$ | 120 | 2.72 × 10$^5$ | 118 |
| surfactant | 24 | 7.1 × 10$^5$ | 95.7 | 1.55 × 10$^5$ | 84 |
| surfactant | 48 | 7.2 × 10$^5$ | 107 | 1.66 × 10$^5$ | 70 |
| surfactant | 72 | 6.6 × 10$^5$ | 89.0 | 1.0 × 10$^5$ | 43 |

*Vero or fetal foreskin cells were incubated with 9 mM n-docosanol suspended in 1.4 mM surfactant or incubated with medium containing 1.4 mM surfactant. The ratio of surfactant to n-docosanol in the suspension was 4:1 (w:w).
**After the indicated time of incubation, cells were trypsinized and the number of viable cells determined by trypan blue exclusion.
***Control samples were incubated in the presence of media only.

cell line and the other cell lines was less than 35 µM; for arachidyl alcohol (C20) the IC$_{50}$ was approximately 1.7 mM. In contrast, the IC$_{50}$ for n-docosanol estimated by extrapolation is approximately 20 mM and is greater than that observed with surfactant alone. Thus, there was about a 50-fold decrease in IC$_{50}$ when the C20 aliphatic alcohol was shortened by 2 carbons.

The data shown in FIG. 5 were obtained after 48 hr of incubation with the suspensions; however, obvious toxicity was apparent within 24 hours of incubation. Suspensions of heneicosanol (C21) and suspensions of the longer chain alcohols, lignoceryl alcohol (C24), n-hexacosanol (C26), and n-octacosanol (C28) showed the same minimal level of cytotoxicity that was seen with the n-docosanol suspensions.

The effects of n-docosanol and n-docosane suspensions on cell proliferation (cytostasis) were quantitated using the sulforhodamine staining assay on cultures of human foreskin fibroblasts incubated in 96-well plates. The results shown in FIG. 6A and 6B demonstrate that the inhibitory effects of the n-docosanol suspension were dependent upon the initial cell density of the in vivo cultures, whereas the n-docosane suspensions showed no significant antiproliferative effect compared to the control surfactant suspension at either cell density. The results shown in FIG. 7 demonstrate that cells associated with the n-docosanol suspension showed greater proliferation inhibition depending on the total incubation period. That is, longer incubation resulted in more inhibition of cell proliferation.

Figure 6B:
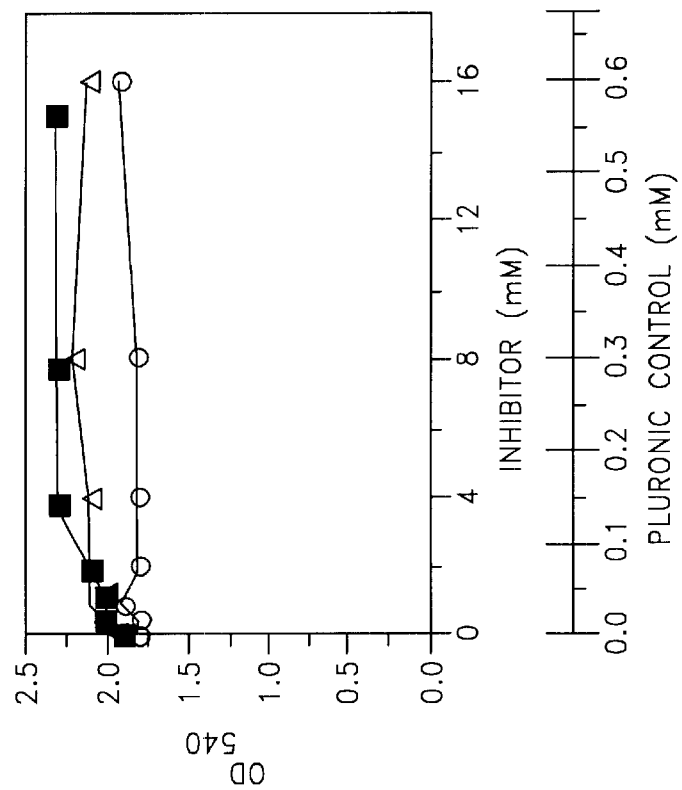
FIG. 6A and FIG. 6B diagrammatically show the cellular antiproliferative effects of suspensions of surfactant/n-docosanol (■) on foreskin fibroblasts compared to cells incubated with suspensions of surfactant/n-docosane (∆) or with controls incubated with a surfactant suspension without active ingredient (○) at the concentrations shown on the X-axes (averages of duplicate assays quantitated after 96 hours incubation of cells inoculated at 1,000 cells/well (FIG. 6A) or 30,000 cells/well (FIG. 6B) in 96-well plates).
Figure 6A:
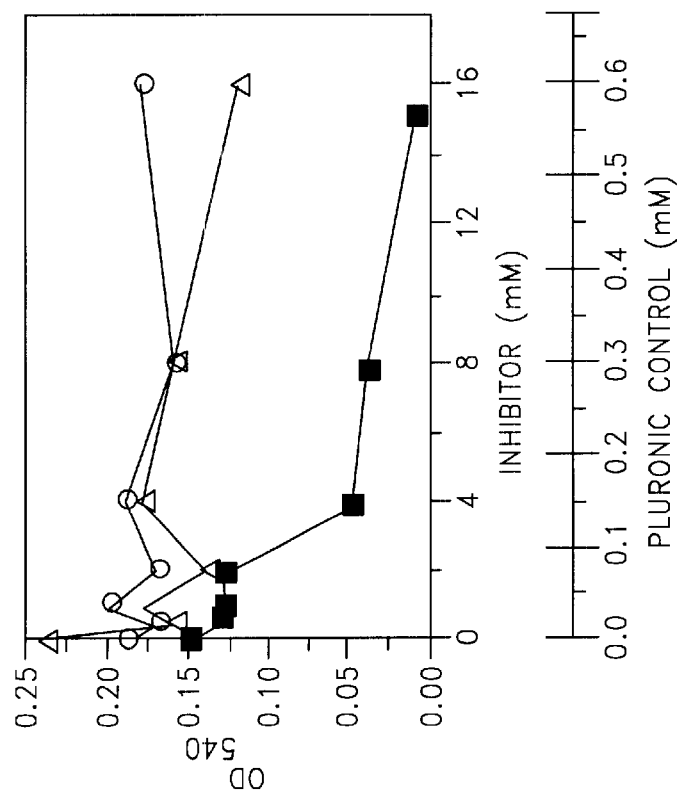
Figure 7:
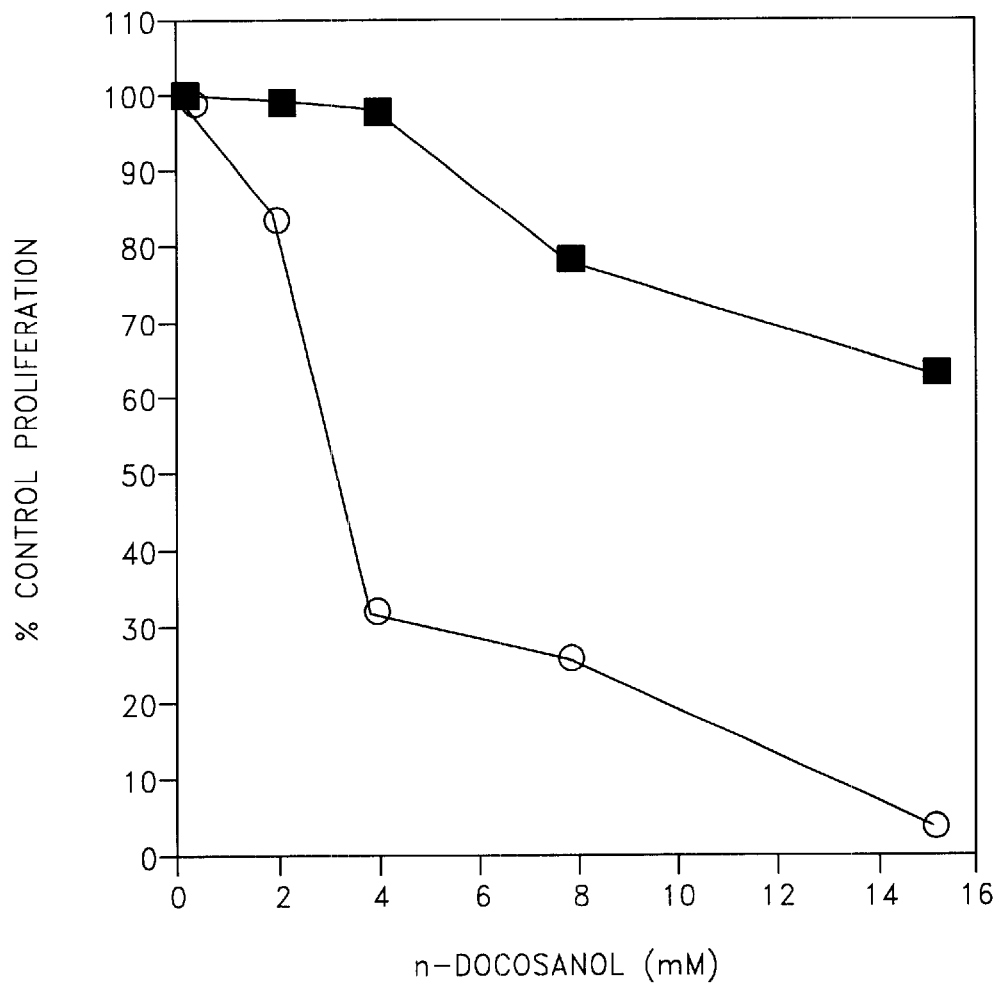
FIG. 7 is a diagram showing the time dependence of cellular antiproliferative effects of surfactant/n-docosanol suspension after 72 hr (■) and 96 hr (○) incubation using the methods as described for FIG. 6A.

Foreskin fibroblasts were plated with or without aliphatic alcohol suspensions or control surfactant suspensions at 1,000 cells/well (FIG. 6A and FIG. 7) or at 30,000 cells/well (FIG. 6B) in 96 well plates. After incubation for 72 hr or 96 hr at 37° C., cells were precipitated with trichloroacetic acid, stained with sulforhodamine and quantitated by measuring the $OD_{540}$ in a microtiter plate reader. FIG. 6 shows the results obtained for cells incubated for 96 hr and FIG. 7 shows the results for cells obtained after 72 hr compared to 96 hr (1000 cells/well).

Suspensions of greater than 3 mM n-docosanol inhibited proliferation of cells plated at 1,000 cells/well assayed after 96-hours incubation (FIG. 6A). In contrast, the suspension of the C22 alkane, n-docosane, showed minimal antiproliferation effects when compared to the surfactant control (FIG. 6A). At higher initial cell densities (FIG. 6B), or shorter times of incubation (FIG. 7), or at concentrations less than 3 mM, n-docosanol did not inhibit cell proliferation compared to the controls (surfactant only in the suspension). Similar results were observed when n-docosanol was incubated with WI-38 cells, human fetal lung cells and normal skin fibroblasts using the same proliferation assay as described for FIGS. 6 and 7.

Suspensions containing aliphatic alcohols greater than C20 exhibited little cellular toxicity. The apparent cytostatic effect was seen only if the cells are plated at low densities and incubated with greater than 3 mM n-docosanol for 72 or more hours. Control suspensions lacking an aliphatic alcohol did not exhibit a cytostatic effect.

Chain length of the aliphatic alcohol affected its cellular toxicity, in contrast to the results presented in Example 1 showing no apparent effect of chain length on antiviral activity. The $IC_{50}$'s decreased from more than 15 mM for C22 or C21 alcohol to 1.5 mM for a C20 alcohol to less than 35 μM for a C18 alcohol. The significant increase in toxicity with an aliphatic alcohol having a chain length only four carbons shorter than the C22 alcohol was unexpected.

EXAMPLE 8

Antiviral Activity of Stearic Acid Compositions

The antiviral activity and cytotoxicity of stearic acid (m.w. 284.5) dissolved in ethanol or suspended in TETRONIC 908®, essentially as described in Example 1, were measured. Antiviral activity was measured as the percentage inhibition of HSV-2 plaque formation in Vero cell culture performed essentially as described in Example 1. Cytotoxicity was assessed by microscopic examination of cells for cell growth and integrity in culture plates compared to untreated control cultures. No apparent toxicity was defined as monolayers of treated cells that were indistinguishable from untreated cells. Moderate toxicity was defined as a thinning of the cell monolayer compared to controls. Toxic was defined as concentrations in which the monolayer of treated cells was destroyed as evidenced by detachment of the cells from the culture plate. No apparent toxicity was observed for 11 μM and 22 μM stearic acid suspensions in TETRONIC 908® and for 3.5 μM stearic acid solution in ethanol. All of these treatments showed less than 10% inhibition of HSV-2 plaque formation relative to infected control cell cultures. Moderate toxicity was observed following treatment with a 44 μM stearic acid-TETRONIC 908® suspension and with 35 μM stearic acid-ethanol solution; antiviral activity could not be quantitated due to condition of the cells. Suspensions and solutions of 88 μM to 350 μM stearic acid were all toxic and antiviral activity could not be determined because the monolayer of cells was destroyed.

EXAMPLE 9

Antiviral Activity of Topically Applied Compositions Containing n-Docosanol or Stearic Acid in an Animal Model The antiviral activity of stearic acid containing compositions was confirmed in vivo using a guinea pig model of HSV-2 infection. Hairless guinea pigs (six males per test, 200–300 g each; from Charles Rivers Laboratories, Wilmington, Mass.) were anesthetized and inoculated with HSV-2 (ATCC strain VR-540, grown in Vero cells and purified using standard methods). On day 0 each animal was inoculated in six inoculation sites within a 4 $cm^2$ area of the back with 75 μl of physiological saline solution containing 9.75×$10^6$ PFU/ml. Beginning at 24 hr post-inoculation (day 1), animals were treated topically three or five times daily with creams described below or water as a negative control and treatments continued at these same rates for days 2, 3 and 4. The inoculation sites were evaluated for skin irritation and vesicle formation daily at days 2, 3 and 4. Irritation was scored on a 0 to 4 scale: 0 for normal skin with no erythema; 1, for mild erythema; 2 for moderate erythema; 3 for severe erythema; and 4, for severe erythema accompanied by bleeding. Vesicles are defined as white, fluid-filled pustules.

The compositions for topical treatment were: an n-docosanol containing cream; a stearic acid containing cream; and a placebo. The n-docosanol cream contained 10% w/w n-docosanol (Michel and Co., New York, N.Y.), 5% w/w sucrose stearate (Croda, Inc., New York, N.Y.), 8% w/w mineral oil NF (Witco Corp., Newark, N.J.), 5% w/w propylene glycol USP, 2.7% w/w benzyl alcohol NF (Ruger Chemical Co., Irvington, N.J.) and 69.3% purified water USP. The stearic acid cream contained 10% w/w stearic acid (Henkel, Cincinnati, OH), 5% w/w sucrose stearate (Croda, Inc., New York, N.Y.), 8% w/w mineral oil NF (Witco Corp., Newark, N.J.), 5% w/w propylene glycol USP, 2.7% w/w benzyl alcohol NF (Ruger Chemical Co., Irvington, N.J.) and 69.3% purified water USP. Both creams were made by combining all the ingredients except water, heating to 80° C., and stirring the ingredients at 400±5 RPM (using a Heidolph RZR 2051 stirrer), to which the water at 85° C. was added while increasing the stirring rate to 1900±5 RPM. After 3 min at 80° C., the mixture was allowed to cool with continuous stirring to 30° C. (about 8 min). The placebo was made by heating 70% polyethylene glycol (PEG) 400 NF and 30% PEG 3350 NF to 65° C. until the PEG 3350 had completely melted, then stirring the mixture at 400 RPM continuously until the mixture had cooled to 30° C.

The results of these tests are summarized as means in Table 4. Determinations at day 2 were made 48 hr post-inoculation; day 3 at 72 hr post-inoculation; and day 4 at 96 hr post-inoculation (total of six sites per determination). As can be seen from Table 4, at day 2, neither cream affected vesicle number significantly relative to the water-treated control and all sites showed no irritation. At day 3, the n-docosanol cream treated sites showed significant inhibition of the number of vesicles relative to the water-treated control. It appears that three applications per day of n-docosanol containing cream are saturating, because five applications per day gave essentially the same level of inhibition. At day 3, sites treated with the stearic acid cream three times per day showed modest vesicle inhibition compared to the water-treated controls, whereas the sites treated five times per day showed statistically significant inhibition of vesicles. Application of the PEG placebo five times per day did not significantly reduce vesicle numbers relative to the water-treated controls at any time point.

At day 3, some irritation was observed with both the n-docosanol and stearic acid creams. At day 4, treatment three times per day with n-docosanol cream significantly reduced the number of vesicles relative to controls, although minor irritation was observed. At day 4, treatment five times per day with n-docosanol cream or stearic acid cream significantly reduced the number of vesicles relative to controls and placebo, although slight erythema was observed with both treatments.

These in vivo results show that topical treatment of HSV-2 infection with creams containing n-docosanol as the active ingredient or stearic acid as the active ingredient can significantly reduce the number of vesicles resulting from the infection. The cream containing n-docosanol as the active ingredient appears to be more effective at treating viral infections because significant reductions in vesicle numbers were seen with only three treatments per day whereas five treatments per day were needed to see reductions in vesicle numbers with the cream containing only stearic acid as the active ingredient.

TABLE 4

Topical Treatment of HSV-2 in Guinea Pig Model

| Treatment | Number of Vesicles | | | Irritation Score | | |
|---|---|---|---|---|---|---|
| | Day 2 | Day 3 | Day 4 | Day 2 | Day 3 | Day 4 |
| Water | 45 | 34 | 19 | 0 | 0 | 0 |
| n-Docosanol (3X/day) | 40 | 12 | 3 | 0 | 1.2 | 0.8 |
| n-Docosanol (5X/day) | 43 | 5 | 3 | 0 | 1.3 | 1.3 |
| Stearic Acid (3X/day) | 49 | 17 | 11 | 0 | 1.2 | 0.8 |
| Stearic Acid (5X/day) | 49 | 13 | 5 | 0 | 1.7 | 2 |
| Placebo (5X/day) | 41 | 30 | 15 | 0 | 0 | 0 |

EXAMPLE 10

Antiviral Activity of Topically Applied n-Docosanol and Stearic Acid in Human Clinical Studies The antiviral activity of stearic acid containing compositions was confirmed in vivo in clinical studies of treatment of oral herpes in 648 immunocompetent patients who initiated treatment within 12 hr of a localized oral herpes episode (i.e., at initial prodrome sensation, erythema or papule but not a vesicle). These patients had a history of acute recurrence of herpes labialis with a reported average duration of untreated episodes lasting 8.9 days (from beginning sensation and/or erythema to complete healing). This duration is consistent with a usual course of 8 to 10 days duration for oral herpes episodes in published reports of the disease (R. J. Whitley, in Fields Virology at p. 2316).

In these studies, patients were randomized to receive either creams containing 10% n-docosanol or 10% stearic acid prepared essentially as in Example 9. Patients applied the cream topically to the localized herpes affected area five times per day for a minimum of five days (25 scheduled applications, with reapplication after heavy exercise, showering or bathing, the reapplications not counted as a scheduled application). If the herpes episode continued after five days, the patients continued to apply the cream up to ten days (50 scheduled applications). The patients kept a diary of application times and lesion pain and itching symptoms and were examined twice per day during the treatment period to assess the effectiveness of treatment.

The criteria used to assess treatment included the time to healing which includes episode abortion (defined as complete resolution of episode-associated symptoms before reaching vesicular stage) or complete healing (defined as absence of crust with no evidence of active lesion, whether or not there was any residual post-lesion skin changes such as erythema, flaking or asymmetry); time to cessation of viral shedding (for study number 1 only); time to reduction in pain; time to cessation of pain; time to cessation of itching; and time to hard crust stage. For comparison, the patients' historical data and published results (Spruance et al., New Eng. J. Med. 297:69–75, 1977) for untreated lesions were used.

Table 5 shows the results of two independent studies (indicated by the numbers in parentheses in the table). These data show that the duration of cold sores decreased significantly to an average of 5.5 days following treatment with either the cream containing n-docosanol or the cream containing stearic acid compared to the patients' reported historical average of 8.9 days duration of untreated cold sores. Thus, the duration was significantly reduced by more than 35% ($P \leq 0.0001$) when patients were treated early in the episode with either the n-docosanol or stearic acid containing cream. Moreover, early-stage treatment with either cream shortened the duration of pain symptoms associated with recurrent herpes episodes from around 6 days when the disease was untreated compared to less than 3 days for treated areas.

EXAMPLE 11

Enhanced Healing of HSV-1 Lesions Following Topical Treatment with n-Docosane Formulation Ten patients with past histories of occurrences of facial HSV-1 lesions (cold sores) are given cream formulations of 5.0 mg/ml n-docosane suspended in 20 mg/ml poloxamer block co-polymer surfactant; the cream formulations include 5–8% by weight mineral oil NF as an emollient, 5% by weight propylene glycol USP as a humectant and preservative, 1–3% by weight benzyl alcohol NF as an auxiliary preservative and the balance purified water as an aqueous carrier.

The individuals are instructed to apply the cream to lesions or early inflammations around the mouth when the individual detects a cold sore. The individuals have a past historical mean of ten days duration for cold sores that were untreated, with all untreated

TABLE 5

Results of Human Clinical Trials
of Topical Treatment of Herpes Labialis.

|  | n-Docosanol Cream Treated | Stearic Acid Cream Treated | Untreated° |
|---|---|---|---|
| Healing Time (hr$^§$) | (1) 123 ± 4.9 | (1) 124 ± 5.2 | (1) 215 ± 0.4 |
|  | (2) 141 ± 5.2 | (2) 143 ± 4.0 | (2) 211 ± 0.4 |
| Cessation of Viral Shedding (hr$^§$) | (1) 47 ± 2.4 (2) ND** | (1) 49 ± 1.9 (2) ND | 74 to 83* |
| Reduction in Pain (hr$^§$) | (1) 27 ± 2.3 (2) 55 ± 4.1 | (1) 31 ± 3.4 (2) 50 ± 3.8 | NR** |
| Complete Cessation of Pain (hr$^§$) | (1) 63 ± 4.4 (2) 96 ± 5.8 | (1) 68 ± 4.5 (2) 86 ± 5.0 | 111 to 178* |
| Cessation of Itching (hr$^§$) | (1) 58 ± 4.9 (2) 63 ± 5.2 | (1) 51 ± 3.4 (2) 76 ± 5.8 | NR |
| Hard Crust Stage (hr$^§$) | (1) 61 ± 3.2 (2) 87 ± 4.4 | (1) 62 ± 2.5 (2) 94 ± 4.9 | NR |

°The healing times are based on the patients' reported histories; all other entries in this column are taken from Spruance et al., New Eng. J Med. 297:69–75, 1977.
$^§$Reported as mean ± standard error of the mean.
*The range represents the median lesion sizes for lesions less than 77.5 mm$^2$ and lesions greater than 77.5 mm$^2$.
***"ND" means "not done" and "NR" means "not reported."

cold sores developing into vesicles that eventually scab and heal. The individuals are instructed to apply the cream to affected areas of the skin at least twice daily and up to four times daily. The individuals are also instructed to record the stages of infection (from erythema to papule to vesicle to edema to scab) that they observe and to record subjective observations about pain associated with the HSV-1 lesions.

Each individual treats at least one cold sore during the course of the study. All individuals report a decrease in pain when the cold sores are treated with the n-docosane containing cream relative to past lesions that were not treated. For each individual, the episode duration of the HSV-1 infection compared to past infections decreases by 20% to 60% (i.e., durations of 4 to 8 days, depending on the individual). In at least half of the individuals participating in the study who treat cold sores four times per day with the n-docosane containing cream, cold sores do not progress to the vesicle stage. Instead, when HSV-1 lesions are topically treated at the erythema or papule stage, the lesions generally do not progress beyond the papule stage and heal without further development of the lesion. These results show that n-docosane containing formulations are effective in preventing and treating viral infections when applied topically.

EXAMPLE 12

Treatment of Influenza Infection with Erucyl Alcohol or Erucamide Formulations

An aqueous suspension of 0.15 mM erucyl alcohol in 1.4 mM of a nonionic poloxamer 188 surfactant containing propylene glycol USP (0.5% by weight) and benzyl alcohol NF (2% by weight) as preservatives is prepared in a standard flexible nasal spray bottle capable of producing an aerosol of the suspension when the bottle is squeezed. Similarly, a preparation containing 1.5 mM erucamide is made and produced in nasal spray containers for producing an aerosol of the suspension. The preparations are provided during the flu season to two groups (one for testing erucyl alcohol and one for testing erucamide) of twenty healthy individuals who have not been inoculated against influenza virus in the previous 12 months.

The individuals are instructed to use the suspension that they are provided as a nasal spray one to five times per day (one to two sprays per nostril at intervals of 2–4 hr) when flu symptoms are detected (respiratory congestion, body aches, sensitive eyes, fever, nausea or any combination of these). Individuals are instructed to record their subjective and objective observations of the severity of their flu symptoms (duration of symptoms, body temperature when feverish, duration and severity of body aches) during the period in which they detect symptoms. The individuals are also instructed to record their use of the nasal spray suspension (number of sprays administered and times of administration) during this period. The individuals are requested to summarize their subjective observations of the severity of their flu symptoms when using the surfactant/erucyl alcohol or surfactant/erucamide aerosol compared to past experiences with influenza infections.

About half of the individuals participating in the study that used the surfactant/erucyl alcohol aerosol as directed report a decrease in flu symptoms relative to previous flu episodes. Those who use the aerosol an average of five times per day (one to two sprays per nostril) report greatly diminished respiratory congestion associated with the influenza infection compared to untreated individuals. Those who use the aerosol an average of five times per day report a significant decrease in the frequency of fever (one to three times per flu episode) compared to untreated individuals (two to five times per flu episode) and a significant decrease in the highest recorded body temperature (mean of 37.8° C.) compared to untreated individuals (mean of 38.9° C.). The mean duration of flu symptoms in about half of the individuals treated with the surfactant/erucyl alcohol aerosol is 1.7 days whereas untreated individuals have a mean duration of flu symptoms of 3 days. These results show that a surfactant/erucyl alcohol suspension has a therapeutic antiviral affect when applied to mucous membranes.

Similar results are obtained with patients treated with the erucamide suspension nasal spray. About half of the patients report a decrease in flu symptoms relative to previous flu episodes when they use the surfactant/erucarnide spray as soon as symptoms were detected. Most individuals experience greatly diminished respiratory congestion when they use the aerosol an average of three times per day (one to two sprays per nostril) compared to previously experienced flu conditions. Most individuals who use the aerosol an average of three times per day report a single fever episode during the flu symptom period with the average highest recorded body temperature at about 37° C. The mean duration of flu symptoms for individuals using the aerosol at least three times daily is two days compared to untreated individuals with a mean duration of flu symptoms of three days. These results show that an aerosol of a surfactant/erucamide suspension has a therapeutic antiviral affect when applied to mucous membranes of the respiratory system.

EXAMPLE 13

Transmucosal Membrane Treatment of HSV-2 Infection with Brassidyl Alcohol

Suppositories containing 8 mM brassidyl alcohol in a nonionic detergent suspension, prepared essentially as in Examples 1 and 5, are formulated by adding anhydrous dextrose (300–400 mg/suppository), vegetable starch (300–400 mg/suppository) and magnesium stearate (5–10 mg/suppository) to produce a mixture that is compressed into suppositories (1–10 g per suppository) for vaginal insertion.

Fifteen HSV-2 infected women with past histories of vaginal and/or perivaginal herpes lesions are provided with the suppositories and instructed to use one to four suppositories per day when herpes lesions or discomfort associated with herpes lesions are detected. The women are instructed to record their observations about the duration of the active infection, the severity of the lesions (erythema, papule, vesicle, edema or scab phases), the relative numbers of lesions detected to past occurrences of active infection, and the subjective degrees of pain or discomfort associated with the active infection episode. The women are instructed to use the suppositories as soon as active infection or symptoms of active infection are detected. The women have a past mean of 12 days duration for lesions that develop into vesicles if untreated.

In all cases, each woman treats at least one episode of active herpes infection during the course of the study. All individuals report a decrease in pain and discomfort when the infection is treated with the suppositories relative to past untreated infection episodes. In all cases, the mean duration of the HSV-2 active infection decreases to 7 to 8 days with suppository treatment with five women reporting a mean duration of 3–4 days. In most cases in which the suppositories were used four times per day and treatment began at the erythema or papule stage, the infection did not progress to the vesicle stage and healed after reaching the papule stage.

Alternatively, the surfactant/brassidyl alcohol suspension is formulated into an ointment containing about 50–80% white soft paraffin which is melted at 60° C. for addition and dispersion of the surfactantibrassidyl alcohol suspension before cooling. The ointment is provided in compressible tubes with the instructions that it be used two to five times daily as needed primarily for external genital treatment of active herpes infections. Individuals are instructed to use a quantity sufficient to cover the HSV-2 lesions in the genital or perivaginal area from one to four times daily as soon as symptoms are detected. At least half of the individuals using the ointment report decreased pain and discomfort, shortened healing time and lesions that do not develop into vesicles before healing.

These results show that surfactant/brassidyl alcohol suspensions have a therapeutic antiviral affect when applied topically to mucous membranes.

EXAMPLE 14

Treatment of EBV Infection (Infectious Mononucleosis) with Long-Chain Aliphatic Alcohol Suspensions Ten young adults (age 14–19 yr) diagnosed with infectious mononucleosis (sore throat, fever, malaise, generalized lymphadenopathy, atypical mononucleosis T-lymphocytes in peripheral blood, a total white cell count of 12,000–18,000 in the blood) are treated systemically with a sterile aqueous suspension of a nonionic detergent surfactant containing 10 mM n-hexacosanol, prepared essentially as in Example 1. The suspension is injected (intramuscular or intravenous) in dosages of 0.1 mg/kg to 0.02 gm/kg of the aliphatic alcohol administered by a physician under clinical conditions. The symptoms of the individuals are then monitored daily for one week and weekly for three months for indications of infectious mononucleosis. All of the individuals test EBV-positive at the end of the study period as determined by detection of anti-EBV antibodies in their serum using standard immunoassays.

All of the individuals show healing of sore throat and fever symptoms within one week of administration of the surfactant/n-hexacosanol suspension and a decrease in the febrile illness symptoms in general within two weeks of administration. Eight of the treated individuals demonstrate a decrease in generalized lymphadenopathy within two to three weeks of administration of the aliphatic alcohol suspension with returned vigor. All treated individuals show a decrease in atypical mononucleosis T-lymphocytes in peripheral blood within four weeks of administration with a normal total white cell count in the blood by two months post-treatment.

Similar results are obtained with EBV-infected individuals showing symptoms of infectious mononucleosis who are treated systemically with suspensions of n-docosanol, lignoceryl alcohol and n-octacosanol at effective concentrations.

These results show that systemic administrations of selected long-chain aliphatic alcohols in aqueous suspensions have a therapeutic antiviral effect.

EXAMPLE 15 n-Docosanol and ACV Exhibit Anti-HSV Activity in Hairless Guinea Pigs

The potential for antiviral interaction with n-docosanol and ACV was investigated in vivo using the cutaneous HSV-2 model in hairless guinea pigs. Skin sites on the backs of hairless guinea pigs were inoculated with HSV-2 with a tattoo instrument. The infected skin sites were treated two times daily as indicated starting 2 hours after virus inoculation. Twice daily treatment, instead of the usual three or five treatment regimen, was chosen because differences could be better observed between the combination cream and single cream formulations, and the vehicle control, which contained stearic acid, does not give a positive response when applied less than 5 times daily.

Figure 8:
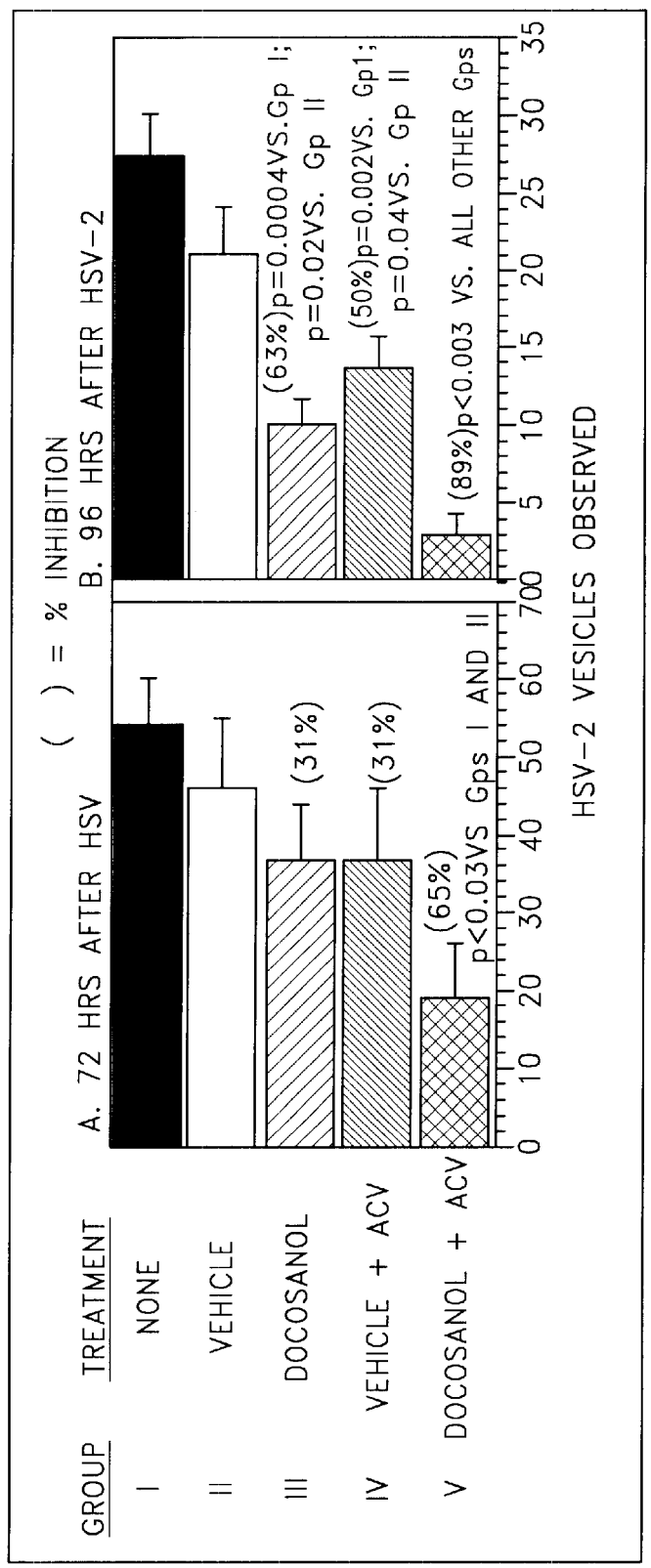
FIG. 8 shows inhibition of HSV-2 cutaneous disease in hairless guinea pigs using a combination cream formulation of n-docosanol plus ACV. The data are mean results from two independently conducted experiments and were analyzed using the student's two-tailed t-test.

HSV-2-induced vesicles were evident by 72 hours post-HSV-2-inoculation (panel A of FIG. 8). The untreated sites exhibited a mean of 54 vesicles at that time point. Vesicle numbers were reduced by 31% with either the n-docosanol cream or the ACV cream, but such inhibition was not statistically significant versus the untreated group. Greater inhibition (65%) was observed with the cream containing both n-docosanol plus ACV, and the mean of 19 vesicles was statistically different from either the untreated or the vehicle-treated groups. Neither n-docosanol nor ACV induced inflammation or toxicity, even when both drugs were concurrently applied.

By 96 hours post-HSV-2-inoculation, the untreated sites exhibited a mean of 27 vesicles. Significant inhibition of vesicle numbers was observed on all treated sites except the vehicle control. Sites treated with the single test formulations of n-docosanol or ACV alone reduced mean vesicle numbers by 63% and 50%, respectively. Even greater inhibitory activity was observed on sites treated with the combination cream of n-docosanol plus ACV, 89% inhibition. The inhibition observed with the combination cream was statistically greater than that observed with the n-docosanol or ACV single test formulations, p=0.003 and p=0.0015, respectively. Again, n-docosanol and ACV induced inflammation or toxicity was not detected, even when used in combination.

Analysis of area under the curve (AUC), defined as the mean number of vesicles times the number of hours vesicles were observed, suggests synergy of the combination of n-docosanol plus ACV. Mean AUC for the untreated group was 698 vesicle hours. Treatment with n-docosanol or ACV alone resulted in respective mean AUC's of 464 (34% inhibition) and 496 (30% inhibition). A theoretical additive effect of n-docosanol plus ACV would have yielded an AUC of 322 (698×remaining fraction after treatment with n-docosanol [0.66]×remaining fraction after ACV treatment [0.7]). The mean AUC for the combination cream was 206 vesicle-hours, 70% inhibition, p=0.01 vs. the theoretical additive effect. Thus, these in vivo observations suggest synergy with n-docosanol plus ACV in the inhibition of HSV-2-induced cutaneous disease, and indicate that n-docosanol and ACV do not interact in vivo, at least cutaneously, in a detrimental manner.

Figure 9:
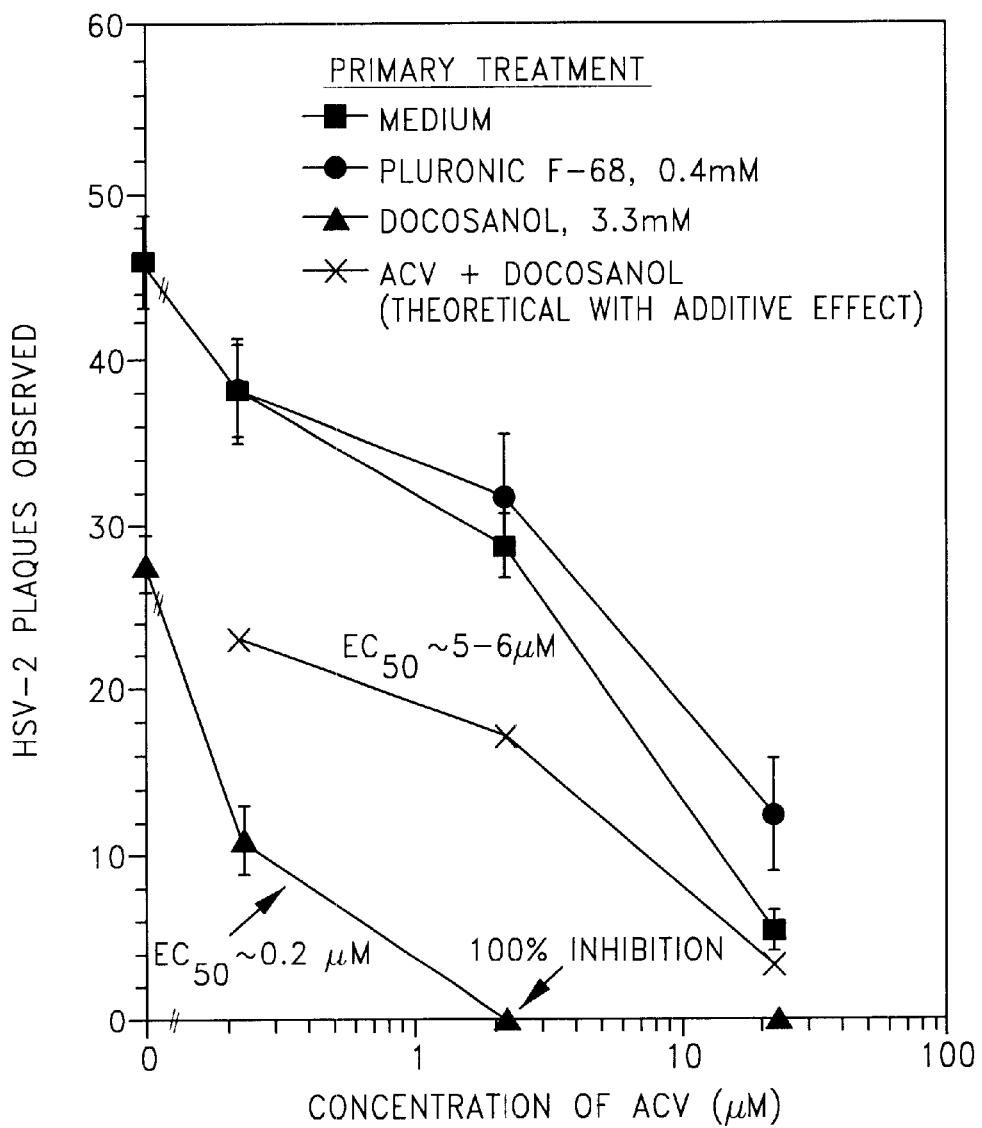
FIG. 9 shows synergistic anti-HSV activity of n-docosanol and ACV in Vero cell cultures. The data are expressed as means and standard errors of plaques observed in triplicate wells/determination.

EXAMPLE 16 n-Docosanol and ACV Exhibit Synergistic Anti-HSV Activity in Vero Cell Cultures The potential for antiviral interaction with n-docosanol plus ACV was investigated more fully in HSV-2-infected Vero cell cultures. Vero cells were cultured in medium alone or in medium containing 3 mM n-docosanol or 0.4 mM PLURONIC F-68® (the amount in the 3 mM n-docosanol culture). The cultures were incubated 24 hours, then exposed to ACV, and infected with 50 plaque forming units of HSV-2; plaque formation was scored 44 hours thereafter. As shown in FIG. 9, the untreated (medium alone) cultures exhibited a mean of 46 plaques and ACV inhibited plaque formation with a 50% effective concentration ($EC_{50}$) of 5 $\mu$M. A similar ACV $EC_{50}$ was obtained with cells cultured in PLURONIC F-68®-containing medium. Cultures that contained n-docosanol exhibited 40% fewer plaques than the untreated or PLURONIC F-68®-treated controls, a reflection of the antiviral activity of the drug. Of particular note, the $EC_{50}$ for ACV in the n-docosanol-containing cultures was reduced to 0.2 $\mu$M. A comparison of the curve for the theoretical additive effect of ACV plus n-docosanol confirms that this 25-fold enhancement of ACV activity was greater than what would be expected with an additive effect. Cellular toxicity, such as cytoplasnic vacuoles, was not observed in the ACV-containing cultures, regardless of the presence or absence of n-docosanol.

EXAMPLE 17

Synergistic Inhibition by n-Docosanol and ACV of HSV-1 Production

The influence of ACV on the n-docosanol $EC_{50}$ for inhibition of HSV-2 plaque formation was also examined. Although not graphically presented, a n-docosanol $EC_{50}$ of 2–3 mM was observed for inhibition of HSV-2 plaque formation when used alone and, when used in conjunction with ACV in the range of 0.2–10 $\mu$M, n-docosanol $EC_{50}$'s of 2–3 mM were observed. As plotted in an isobologramn (not shown), these results suggest that ACV has little effect on the antiviral activity of n-docosanol, even though the latter drug substantially enhanced the activity of the former.

Significant reduction of the ACV $EC_{50}$ by n-docosanol was also observed in the inhibition of HSV-1 plaque formation (not shown). This was associated with a substantial reduction in the ACV $EC_{90}$ for inhibition of progeny HSV-1 (panel A of FIG. 10). Vero cells were treated as before with the indicated concentrations of n-docosanol, PLURONIC F-68®, and ACV and infected with HSV-1 (500 PFU per culture, 0.002 PFU/cell). The culture supernatants were harvested 72 hours thereafter and assayed for HSV-1. ACV $EC_{90}$'s of 10 $\mu$M for inhibition of HSV-1 production were observed in cultures containing medium only or medium plus PLURONIC F-68®. n-Docosanol at a concentration of 3.3 mM inhibited PFU production by 55% and lowered the ACV $EC_{90}$ by 17-fold. Greater synergy was observed with 10 mM n-docosanol (FIG. 10), where the EC90 was reduced 40-fold. The synergy which was even more pronounced with 30 mM of the drug (ACV $EC_{90}$<0.1 $\mu$M, not shown).

To further confirm that the effects of combining n-docosanol plus ACV were synergistic, the data were charted in an isobologram (panel B of FIG. 10). The broken line extending diagonally shows the theoretical plot for independent inhibitors, displacement of the curve to the left indicates synergistic interaction, while displacement to the right would indicate antagonism (Spector et al., *Proc. Natl. Acad. Sci. USA* 86:1051–1055, 1989). It is clear that the experimental observations for HSV-1 PFU production indicate synergy with the drug combination of n-docosanol plus ACV.

EXAMPLE 18 n-Docosanol and ACV Synergize to Inhibit Replication of Human Varicella Zoster Virus (VZV) and Cytomegalovirus (CMV) in MRC-5 cells The results shown in Table 6 make two important points. First, it was observed that the synergistic activity of n-docosanol plus ACV was not dependent on the use of Vero cells and could also be documented with the normal human MRC-5 fibroblastic cell line. Second, it was observed that such activity was not restricted to HSV, but could also be demonstrated in the inhibition of human VZV and CMV replication. VZV- and CMV-induced diseases tend to be relatively resistant to therapy with ACV (Hirsch et al., In *Fields Virology* Third Edition, B. N. Fields, D. M. Knipe, P. M. Howley, eds. Lippincott-Raven Publishers, Philadelphia, pp. 431–466, 1996). Thus, n-docosanol-mediated enhancement of ACV antiviral activity could be clinically significant.

As shown by groups I–V of Table 6, 350,000 VZV-infected cells could be detected in the medium alone cultures four days following infection of MRC-5 cells with 500 PFU of VZV. ACV inhibited VZV infection with an $EC_{50}$ of 3 $\mu$M and an $EC_{90}$ of 10 $\mu$M. VZV replication was inhibited by n-docosanol with an $EC_{50}$ of approximately 10 mM. ACV $EC_{50}$'s and $EC_{90}$'s were reduced 90% and 80%, respectively, with the high 30 mM concentration of n-docosanol.

Similar results were obtained with CMV (groups VI–X, Table 6). Four days following infection of MRC-5 cells with 500 PFU of CMV, 200,000 infected MRC-5 cell could be detected in control cultures and ACV inhibited such infection with an $EC_{50}$ and $EC_{90}$ of 30 and 250 $\mu$M, respectively. n-Docosanol inhibited CMV replication with an $EC_{50}$ of about 10 mM. ACV $EC_{50}$'s and $EC_{90}$'s for inhibition of CMV replication were reduced 90% with n-docosanol concentrations of 10–30 mM.

EXAMPLE 19

Figure 11:
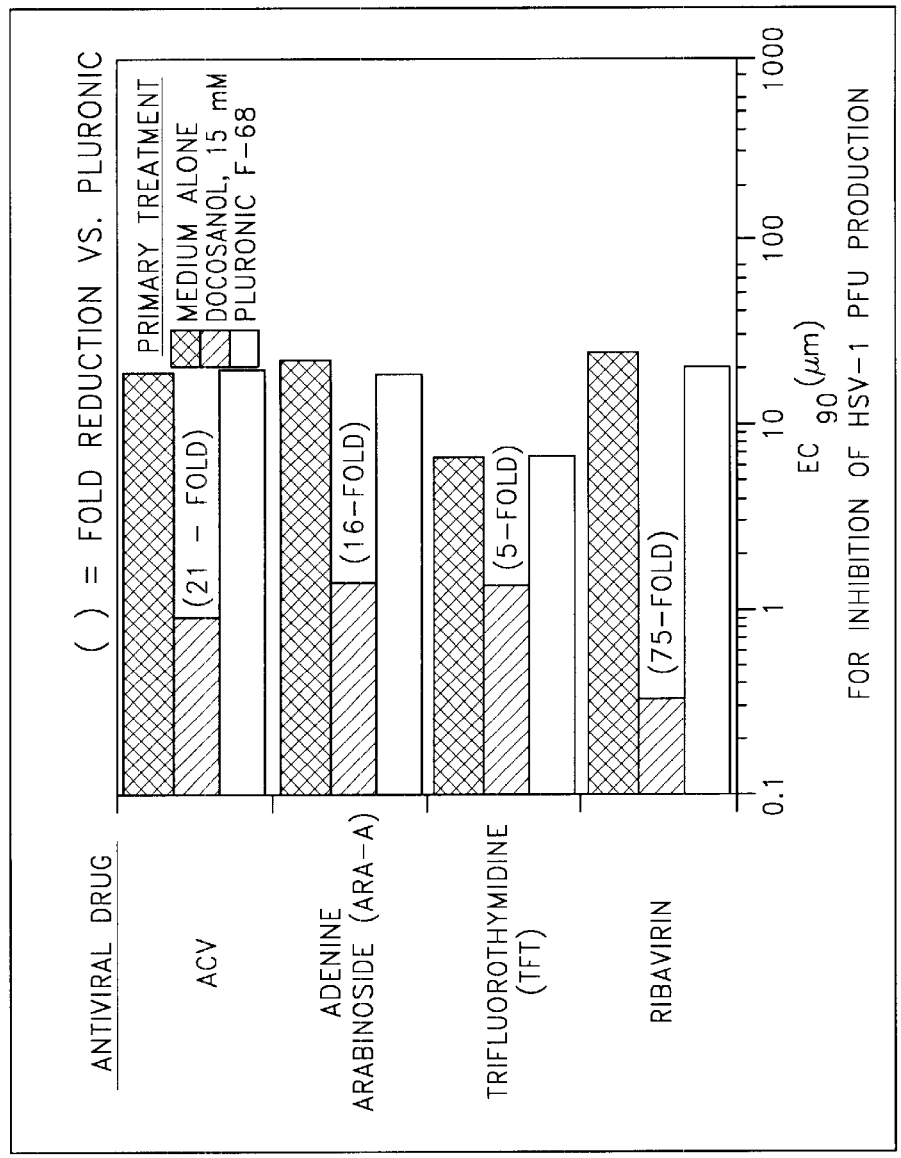
FIG. 11 shows synergistic inhibition of HSV-1 replication in vitro by n-docosanol and nucleoside analogs other than ACV. The data are expressed as the $EC_{90}$ for inhibition of HSV-1 production derived from mean PFU observed in triplicate initial cell cultures/determination.

Nucleoside Analogs Other than ACV Also Synergize with n-Docosanol to Inhibit HSV-1 Replication In vivo It was of interest to determine if antiviral synergy with n-docosanol was restricted to ACV, or whether other nucleoside analogs, could also interact with n-docosanol. The issue was investigated with HSV-1 PFU production in Vero cell cultures (FIG. 11). Untreated, n-docosanol-treated (15 mM) and PLURONIC F-68®-treated Vero cells were

TABLE 6 n-Docosanol and ACV Synergize to Inhibit Replication of Varicella Zoster Virus (VZV) and Cytomegalovirus (CMV) in MRC-5 Cell Cultures

| Group | MRC-5 Cultures | Virus | IC per Culture × $10^{-4}$ ( ) = % Inhibition | ACV Efficacy $EC_{50}$ ($\mu$M) | $EC_{90}$ ($\mu$M) |
|---|---|---|---|---|---|
| I | Medium Only | VZV | 35 | 3 | 10 |
| II | n-Docosanol, 30 mM | " | 7 (80%) | 0.3 | 2 |
| III | n-Docosanol, 10 mM | " | 15 (57%) | 0.6 | 4 |
| IV | n-Docosanol, 3.3 mM | " | 21 (40%) | 1 | 6 |
| V | Pluronic F-68 | " | 33 (6%) | 3 | 10 |
| VI | Medium Only | CMV | 20 | 30 | 250 |
| VII | n-Docosanol, 30 mM | " | 3 (85%) | 2 | 6 |
| VIII | n-Docosanol, 10 mM | " | 8 (60%) | 2 | 25 |
| IX | n-Docosanol, 3.3 mM | " | 16 (20%) | 8 | 35 |
| X | Pluronic F-68 | " | 20 (0%) | 30 | 250 |

MRC-5 cell cells were cultured (16-mm wells, $10^5$ cells/ml, 1 ml/well) in medium alone, or in medium containing 30, 10, or 3.3 mM n-docosanol or that amount of Pluronic F-68 contained in the 30 mM n-docosanol cultures. After overnight incubation, acyclovir was added at varied concentrations and the cultures were infected with VZV (Groups I—V) or CMV (Groups VI–X). After 2 days incubation medium lacking n-docosanol, Pluronic F-68, or acyclovir was added to all the cultures. After an additional 2 days, cells from the cultures were harvested and assayed for infected cells (IC) by an infectious center assay. Infected cell data are expressed as mean infected cells/culture derived from quadruplicate (VZV) or triplicate (CMV) wells per initial culture group. (Ref. JM 1290, 460L-134/9-23-96) rvsd 4-4-97 infected with 500 PFU/culture of HSV-1 and exposed to varied concentrations of the indicated nucleoside analog antiviral drugs. Three days later, the culture supernatant fluids were harvested and analyzed for progeny HSV-1 PFU. A typical ACV anti-HSV-1 $EC_{90}$ of 19 $\mu$M was observed in control cultures, which was reduced to 0.9 $\mu$M (a 21-fold reduction) in the presence of n-docosanol. The nucleoside analog adenine arabinoside (Ara-A) exhibited an $EC_{90}$ of about 22 $\mu$M when used alone and an $EC_{90}$ of about 1.4 $\mu$M (a 16-fold reduction) when n-docosanol was included in the culture. Trifluridine exhibited an $EC_{90}$ of about 6.8 $\mu$M in the absence of n-docosanol and an $EC_{90}$ of about 1.35 $\mu$M (a 5-fold reduction) when both drugs were present. Similarly, ribavirin when used alone inhibited HSV-1 replication with an $EC_{90}$ of about 24.6 $\mu$M, which was reduced to approximately 0.33 $\mu$M (a 75-fold reduction) in the presence of n-docosanol. Although not shown, rifampicin did not inhibit HSV replication regardless of the presence or absence of n-docosanol.

EXAMPLE 20 n-Docosanol and Phosphonoforrnic Acid (PFA) Exhibit Additive Antiviral Activity Against HSV-1 Replication The potential for antiviral interaction between n-docosanol and PFA, an organic analog of inorganic pyrophosphate, is presented in FIG. 12. As shown in panel A, untreated Vero cell cultures produced about $10^7$ PFU of HSV-1 three days post-infection and PFA inhibited such PFU production with an $EC_{90}$ of about 18 $\mu$M. Similar levels of PFU production and PFA-mediated inhibition were observed with cultures treated with the vehicle control, PLURONIC F-68®. Cultures treated with 15 mM n-docosanol alone exhibited approximately 10-fold fewer HSV-1 PFU and PFA further decreased PFU production with an $EC_{90}$ of 17 $\mu$M. The combined effects of n-docosanol plus PFA coincide with the line for the theoretical additive effects.

Panel B of FIG. 12 illustrates two points. First, the results from cultures that lacked PFA show the n-docosanol does not inhibit replication of vaccinia virus; 5–6×$10^5$ PFU of vaccinia virus were produced regardless of the presence or absence of n-docosanol or PLURONIC F-68®. Second, the presence or absence of n-docosanol or PLURONIC F-68® did not enhance or inhibit the antiviral activity of PFA against vaccinia virus replication, i.e., there was no drug-drug interaction with this particular virus.

Figure 13:
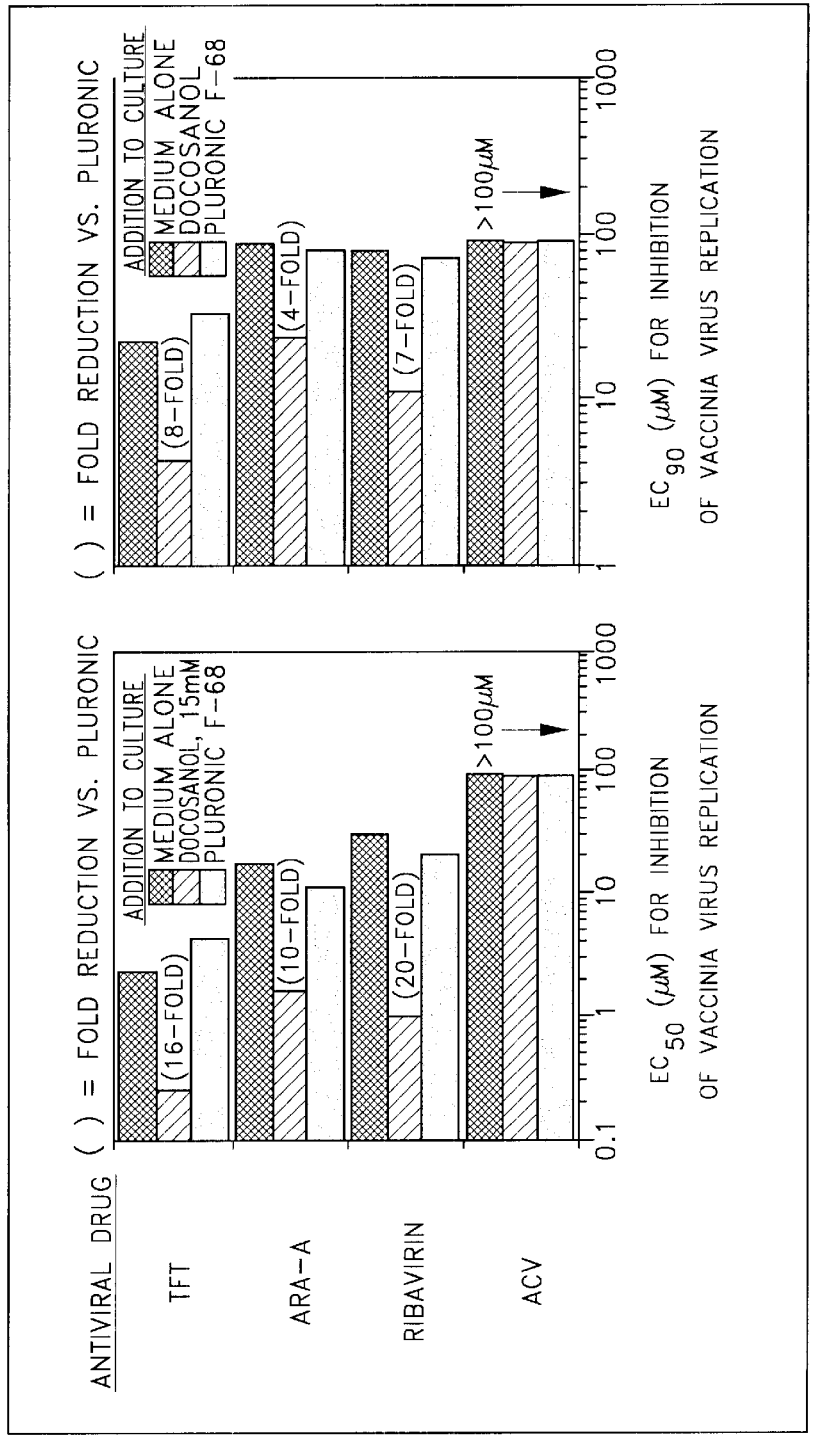
FIG. 13 shows enhancement by n-docosanol of the antiviral activity of nucleoside analogs on vaccinia virus replication. The data are expressed as the $EC_{50}$ (panel A) or $EC_{90}$ (panel B) for inhibition of HSV-1 production derived from mean PFU observed in triplicate initial cell cultures.

EXAMPLE 21 n-Docosanol Increases the Inhibition of Vaccinia Virus Replication by Nucleoside Analogs Since vaccinia virus is insensitive to the antiviral effects of n-docosanol, it was possible to investigate the relationship between the antiviral activity of the n-docosanol and synergy with nucleoside analogs. As previously described for panel B of FIG. 12, untreated Vero cells exhibited a mean production of 5–6×$10^5$ PFU of progeny vaccinia virus 3 days post-infection, regardless of the presence or absence of n-docosanol or PLURONIC F-68®. As shown in panel A of FIG. 13, vaccinia virus replication in control cultures (medium or PLURONIC F-68®) was inhibited by trifluridine, Ara-A, and ribavirin with $EC_{50}$'s of approximately 2, 20, and 25 $\mu$M, respectively. The $EC_{50}$ for each of these nucleoside analogs was reduced at least 10-fold in cultures containing 15 mM n-docosanol. Vaccinia virus is normally insensitive to the antiviral effects of ACV, and treatment of cells with n-docosanol did not change this selectivity. Panel B of FIG. 13 presents the $EC_{90}$'s for these same nucleoside drugs and comparable conclusions can be derived from the results. These data indicate that a virus does not have to be sensitive to the antiviral activity of n-docosanol in order for n-docosanol to increase the antiviral activity of nucleoside analogs against that virus.

In summary, n-docosanol did not exhibit a detrimental drug-drug interaction with ACV in any test system. Cutaneous irritation of guinea pig skin was not observed when the two drugs were applied alone or in combination. Guinea pig skin tends to exhibit more sensitivity to irritation than human skin, suggesting that treatment of patients concurrently with n-docosanol plus ACV will also not elicit irritation. Cellular toxicity in vitro was also not observed with the two drugs, either alone or in combination. Rather, n-docosanol substantially enhanced the anti-HSV activity of ACV in vitro and in vivo. This enhancement was synergistic in vitro. These results suggest that concomitant treatment of recurrent HSV disease with n-docosanol plus ACV would be a highly beneficial therapeutic strategy.

Antiviral synergy with n-docosanol plus ACV was not limited to HSV-1 and HSV-2, but was also observed with VZV and CMV. These latter results are reasonable since all of these herpesviruses are sensitive to ACV (Hirsch et al., In Fields Virology Third Edition, B. N. Fields, D. M. Knipe, P. M. Howley, eds. Lippincott-Raven Publishers, Philadelphia, pp. 431–466, 1996), albeit to varying degrees. Such synergy was also observed with the other tested nucleoside analogs that inhibit HSV replication. This would be expected since the different nucleoside or nucleotide analogs tend to use common cellular and viral mechanisms for transport across the plasma membrane, metabolic activation, and antiviral expression. Since VZV and CMV have replication steps in common with HSV, it is probable that n-docosanol will also synergize with nucleoside analogs other than ACV to inhibit these viruses too.

n-Docosanol synergized with certain tested nucleoside analogs in the inhibition of vaccinia virus replication. Vaccinia virus replication is not inhibited by n-docosanol, indicating that a virus need not be susceptible to n-docosanol to observe synergy with a second class of drug. This is an important result for two reasons. First, comparison of the vaccinia virus response with that of herpesvirus could give information as to the molecular mechanisms for such synergy. Second, and more importantly, this suggests that the use of n-docosanol need not be restricted to the treatment of diseases caused by viruses that are sensitive to the antiviral effects of the drug. These results also indicate that n-docosanol may be used to enhance nucleoside analog activity independently of virus infection to treat other diseases such as inflammation, autoimmunity, and cancer.

The antiviral selectivity of the tested nucleoside and nucleotide analogs did not seem to change with n-docosanol treatment. The selectivity of an antiviral drug like ACV is dependent on a characteristic of the virus, such as expression of virally-encoded thymidine kinase. This explains the lack of inhibition by ACV on vaccinia virus replication regardless of the presence or absence of n-docosanol.

The extent to which n-docosanol can interact with a given antiviral drug on a given class of virus will have to be determined empirically. Antiviral synergy with PFA and n-docosanol was not observed with HSV or vaccinia virus indicating this will not occur with all antiviral compounds. Certain predictions are possible however, such as antiviral synergy with n-docosanol plus nucleoside analogs such as AZT in the inhibition of HIV replication. Influenza virus and respiratory syncytial virus are also likely candidates for this nucleoside analog/n-docosanol synergistic response.

Regardless of the mechanisms underlying the synergistic antiviral activity of n-docosanol and ACV, there are several advantages to a strategy of combination therapy with nucleoside or nucleotide analogs plus n-docosanol. First, combination therapy in general has proven to be highly effective by recent successes in treatment of HIV infections and cancer. A common feature of such therapy is the use of two or more drugs having uncommon mechanisms of action. Even without synergistic antiviral activity, combination therapy of recurrent HSV disease with n-docosanol plus ACV would be advantageous based on their non-overlapping mechanisms of action. Nevertheless, n-docosanol does exhibit synergistic antiviral activity with nucleoside analogs, perhaps by causing the virus-infected cell to concentrate enhanced levels of the drugs. Therefore, a second advantage of concurrently using a safe drug like n-docosanol would be the ability to selectively target a cell population and increase efficacy of nucleoside or nucleotide analogs, shorten healing time, lessen the likelihood of selection of drug-resistant mutants, and reduce patient exposure to potentially toxic and allergenic nucleoside drugs.

A logical application of combination nucleoside analog and n-docosanol therapy would be to use a homogenous cream, ointment, or suspension mixture of the drugs. This type of application worked well in the animal studies (FIG. 8) and may be used with ACV in the treatment of patients with recurrent HSV diseases. Herpesvirus-related diseases like shingles, CMV retinitis, or Kaposi's sarcoma may also respond better to nucleoside therapy in the presence of n-docosanol. Virtually any diseased tissue that could be treated with a cream or suspension formulation of n-docosanol could be targeted for enhanced nucleoside therapy in this manner, including the skin, the GI tract, the respiratory system, and certain organs of the reproductive system. An extension of this application would be systemic administration of a nucleoside or nucleotide analog and local treatment with n-docosanol. Assuming that an approved systemic formulation of n-docosanol is developed, systemic n-docosanol and nucleoside or nucleotide analog combination therapy could target virtually any organ in the body.

The use of n-docosanol to concentrate nucleoside analogs to diseased tissue may not be restricted to those caused by viruses. It remains to be determined whether combination n-docosanol/nucleoside therapy would function with unmanipulated cancer cells. However, there has been recent interest in the use of gene transfer technology for the treatment of cancer using virally-encoded genes and antiviral nucleoside drugs; n-docosanol could ultimately have a role in this strategy. Indeed, transfection of melanoma cells with the HSV thymidine kinase gene rendered the cells sensitive to the toxic effects of the normally HSV-selective nucleoside drug ganciclovir (Oliver et al., Virol. 145:84–93, 1985). It is possible that treatment of the skin cancer cells with n-docosanol would intensify the response. Virus diseases that are difficult to treat could also be targeted in this manner, since a similar response was observed using suicide gene therapy and nucleoside analogs on Epstein-Barr virus-infected human B lymphoma cells (Franken et al., *Nature Medicine* 2:1379–1382, 1996) and on HIV-1-infected human T cells (Caruso et al., Virol. 206: 495–503, 1995).

The disclosed method for treating viral infections comprises the administration of a long-chain aliphatic compound in conjunction with a nucleoside or nucleotide analog or PFA. Preferably, the active ingredients are co-administered. In another embodiment, the active ingredients are mixed together and administered in a pharmaceutically acceptable carrier. As used herein, administration of an aliphatic compound in conjunction with a nucleoside analog or PFA means that the compounds may be administered to one patient at different times and according to different dosage and treatment regimens, but wherein the treatment regimens produce overlapping in vivo concentrations of both compounds, thereby facilitating the beneficial interactions between the two classes of drugs. Co-administration of an aliphatic compound and a nucleoside analog means that the two active agents are administered at the same time, though not necessarily via the same route.

The aliphatic compound may be administered from one to five times daily via topical, oral, mucosal, transmembranal penetration and intravenous routes. Similarly, the nucleoside analog or PFA may also be administered from one to five times daily via topical, oral, mucosal, transmembranal penetration and intravenous routes. Preferably, the aliphatic compound is applied locally to the diseased tissue, and the nucleoside analog is administered systemically. The dosages of the active aliphatic compounds in accordance with the present invention is from 0.05% to about 40%. Most preferably, the aliphatic compounds are used at a concentration in the range of about 1% to about 20%.

The synergistic interaction of n-docosanol and nucleoside analogs may be exploited using a regimen of systemic nucleoside analog administration coupled with local n-docosanol application to the diseased tissue. For example, oral acyclovir at a dose of 500 mg given 5 times a day attained a maximum average acyclovir plasma concentration of approximately 0.7 $\mu$g/ml (Tyring et al., Arch Dermatol 134:185–191, 1998). Oral valacyclovir given twice daily at a dose of about 1000 mg each attained a maximum acyclovir plasma concentration of approximately 4.3 $\mu$g/ml. Infusion of acyclovir suspension at a dose of 5 mg/kg by 1-hour infusions every 8 hours attained a steady state acyclovir plasma concentration of approximately 10 $\mu$g/ml (Blum et al., $\mu$Am. J. Med. 73:186–192, 1982). These dosage schemes in conjunction with concurrent one to five times daily administration of n-docosanol topically, orally, via the urogenital tract (mucosally), transmembranally or intravenously should effectively exploit the beneficial interactions between the two classes of drugs.

Although the present invention has been described in the context of particular examples and preferred embodiments, it will be understood that the invention is not limited to such embodiments. Instead, the scope of the present invention shall be measured by the claims that follow.

What is claimed is:

1. A synergistic antiviral composition, comprising a C21–C28 aliphatic alcohol, a nucleoside analog or nucleotide analog selected from the group consisting of acyclovir, adefovir, azidothymidine, brivudin, cidofovir, ddC, ddI, famciclovir, ganciclovir, idoxuridine, lamivudine, lobucavir, penciclovir, ribavirin, sorivudine, trifluridine, valaciclovir and Ara A, and a pharmaceutical acceptable carrier.

2. The composition of claim 1, wherein the aliphatic alcohol is selected from the group consisting of primary alcohols, and mixture thereof.

3. The composition of claim 1, wherein the aliphatic alcohol is present at a concentration in a range of about 0.05% to about 40%.

4. The composition of claim 1, wherein the aliphatic alcohol is selected from the group consisting of erucyl alcohol, brassidyl alcohol, n-docosanol, and mixtures thereof.

5. The composition of claim 1, wherein the nucleoside analog or nucleotide analog is present at a concentration in a range of about 0.1% to about 10%.

6. The composition of claim 1, further comprising a nonionic surfactant.

7. The composition of claim 6, wherein the nonionic surfactant comprises a difunctional block-polymer that is a polyoxyalkylene derivative of propylene glycol having a molecular weight of about 1,000 to about 25,000.

8. The composition of claim 6, wherein the nonionic surfactant comprises a block copolymer of ethylene oxide and propylene oxide having a molecular weight of between 6,000 and 12,000.

9. The composition of claim 6, wherein the nonionic surfactant is selected from the group consisting of octoxynol-9 and octoxynol-10.

10. The composition of claim 6, further comprising a penetration enhancer.

11. The composition of claim 1, further comprising other agents selected from the group consisting of anti-microbial agents, other antiviral agents, anti-fungal agents, antioxidants, buffering agents, sunscreens, cosmetic agents, fragrances, lubricants, moisturizers, drying agents, and thickening agents.

12. The composition of claim 1, wherein said aliphatic alcohol is n-docosanol.

13. The composition of claim 12, wherein the n-docosanol is present at a concentration in a range of about 0.05% to about 40%.

14. The composition of claim 12, wherein the nucleoside analog or nucleotide analog is present at a concentration in a range of about 0.1% to about 10%.

15. The composition of claim 12, further comprising a nonionic surfactant.

16. The composition of claim 15, wherein the nonionic surfactant comprises a difunctional block-polymer that is a polyoxyalkylene derivative of propylene glycol having a molecular weight of about 1,000 to about 25,000.

17. The composition of claim 15, wherein the nonionic surfactant comprises a block copolymer of ethylene oxide and propylene oxide having a molecular weight of between 6,000 and 12,000.

18. The composition of claim 15, wherein the nonionic surfactant is selected from the group consisting of octoxynol-9 and octoxynol-10.

19. The composition of claim 15, further comprising a penetration enhancer.

20. The composition of claim 12, further comprising other agents selected from the group consisting of anti-microbial agents, other antiviral agents, anti-fungal agents, antioxidants, buffering agents, sunscreens, cosmetic agents, fragrances, lubricants, moisturizers, drying agents, and thickening agents.

21. A composition for treatment or prophylaxis of a viral infection, comprising a mixture of n-docosanol and an antiviral agent selected from the group consisting of acyclovir, ribavirin, trifluridine and Ara A.

22. The composition of claim 21, wherein the n-docosanol is present at a concentration in a range of about 0.05% to about 40%.

23. The composition of claim 21, wherein the antiviral agent is present at a concentration in a range of about 0.1% to about 10%.

24. The composition of claim 21, further comprising a pharmaceutically acceptable carrier that comprises sucrose stearate in a concentration of about 1% to about 25%, mineral oil in a concentration of about 1% to about 25%, propylene glycol USP in a concentration of about 1% to about 25%, benzyl alcohol in a concentration of about 0.1% to about 10%, and water.

25. A method for treatment or prophylaxis of a viral infection, comprising administration of n-docosanol in conjunction with an antiviral agent selected from the group consisting of acyclovir, ribavirin, trifluridine, and Ara A.

26. A method for treatment or prophylaxis of a viral infection, comprising the administration of a synergistic combination of a C21–C28 aliphatic alcohol, and an antiviral agent selected from the group consisting of acyclovir, adefovir, azidothymidine, brivudin, cidofovir, ddC, ddI, famciclovir, ganciclovir, idoxuridine, lamivudine, lobucavir, penciclovir, ribavirin, sorivudine, trifluridine, valaciclovir and Ara A.

27. The method of claim 26, wherein said C21–C28 aliphatic alcohol is selected from the group consisting of primary alcohols, and the mixture thereof.

28. The method of claim 26, wherein said C21–C28 aliphatic alcohol is selected from the group consisting of erucyl alcohol, brassidyl alcohol n-docosanol, and mixtures thereof.

29. The method of claim 26, wherein the aliphatic alcohol is co-administered with the antiviral agent.

30. The method of claim 26, wherein the aliphatic alcohol is administered one to five times per day via a route selected from the group consisting of topical, oral, mucosal, transmembranal penetration and intravenous, and wherein the antiviral agent is administered one to five times per day.

31. The method of claim 30, wherein the antiviral agent is administered via a route selected from the group consisting of topical, oral, mucosal, transmembranal penetration and intravenous.

32. The method of claim 26, wherein the aliphatic alcohol and the antiviral agent are administered together in a composition further comprising a pharmaceutically acceptable carrier.

33. The method of claim 32, wherein the composition further comprises a nonionic surfactant.

34. The method of claim 32, wherein the composition further comprises a penetration enhancer.

35. The method of claim 32, wherein a dose of about 0.01 to about 10 grams of the composition is administered with a frequency of about one to five times per day for a period of about one to fourteen days.

36. The method of claim 32, wherein the composition is administered via a route selected from the group consisting of topical, oral, mucosal, transmembranal penetration and intravenous.

37. The method of 26, wherein the said aliphatic alcohol is erucyl alcohol, and the said antiviral agent is selected from the group consisting of acyclovir, ribavirin, trifluridine, and Ara A.

38. A method for treatment or prophylaxis of a viral infection, comprising the administration of a synergistic combination of n-docosanol, and an antiviral agent selected from the group consisting of acyclovir, adefovir, azidothymidine, brivudin, cidofovir, ddC, ddI, famciclovir, ganciclovir, idoxuridine, lamivudine, lobucavir, penciclovir, ribavirin, sorivudine, trifluridine, valaciclovir and Ara A.

39. The method of claim 38, wherein the n-docosanol is co-administered with the antiviral agent.

40. The method of claim 38, wherein the n-docosanol is administered one to five times per day via a route selected from the group consisting of topical, oral, mucosal, transmembranal penetration and intravenous, and wherein the antiviral agent is administered one to five times per day.

41. The method of claim 40, wherein the antiviral agent is administered via a route selected from the group consisting of topical, oral, mucosal, transmembranal penetration and intravenous.

42. The method of claim 38, wherein the n-docosanol and the antiviral agent are administered together in a composition further comprising a pharmaceutically acceptable carrier.

43. The method of claim 42, wherein the composition further comprises a nonionic surfactant.

44. The method of claim 42, wherein the composition further comprises a penetration enhancer.

45. The method of claim 42, wherein a dose of about 0.01 to about 10 grams of the composition is administered with a frequency of about one to five times per day for a period of about one to fourteen days.

46. The method of claim 42, wherein the composition is administered via a route selected from the group consisting of topical, oral, mucosal, transmembranal penetration and intravenous.

* * * * *